(12) United States Patent
Werner et al.

(10) Patent No.: US 8,624,080 B2
(45) Date of Patent: Jan. 7, 2014

(54) PLANT VIRUS-BASED INDUCIBLE EXPRESSION SYSTEM

(75) Inventors: Stefan Werner, Saale (DE); Sylvestre Marillonnet, Saale (DE); Victor Klimyuk, Saale (DE); Yuri Gleba, Saale (DE)

(73) Assignee: Icon Genetics GmbH, Munich (DE)

( * ) Notice: Subject to any disclaimer, the term of this patent is extended or adjusted under 35 U.S.C. 154(b) by 743 days.

(21) Appl. No.: 12/301,156

(22) PCT Filed: May 25, 2007

(86) PCT No.: PCT/EP2007/004688
§ 371 (c)(1),
(2), (4) Date: Apr. 21, 2009

(87) PCT Pub. No.: WO2007/137788
PCT Pub. Date: Dec. 6, 2007

(65) Prior Publication Data
US 2009/0282579 A1    Nov. 12, 2009

Related U.S. Application Data

(60) Provisional application No. 60/810,398, filed on Jun. 2, 2006.

(30) Foreign Application Priority Data

May 29, 2006    (EP) .................................... 06011002

(51) Int. Cl.
| C12N 15/40 | (2006.01) |
|---|---|
| C12N 15/79 | (2006.01) |
| C12N 15/83 | (2006.01) |
| C12N 7/01 | (2006.01) |
| A01H 5/00 | (2006.01) |

(52) U.S. Cl.
USPC ......... 800/280; 435/419; 435/468; 536/23.72

(58) Field of Classification Search
USPC ....................................................... 800/278
See application file for complete search history.

(56) References Cited

U.S. PATENT DOCUMENTS 7,667,092 B2 *    2/2010    Klimyuk et al. .............. 800/278

FOREIGN PATENT DOCUMENTS

| EP | 1 564 295 A | 8/2005 |
|---|---|---|
| WO | WO 2005/049839 A2 | 6/2005 |
| WO | WO 2006/003018 A2 | 1/2006 |

OTHER PUBLICATIONS

Hull, R. Mathews Plant Virology, Fourth Edition (2002) Academic Press: London pp. 183-194.*
Mori, M., Fujihara, N., Mise, K., Furusawa, I. Inducible high-level mRNA amplification system by viral replicase in transgenic plants. (2001) The Plant Journal. 27: 79-86.*
Mallory, A., Parks, G., Endres, M.W., Baulcombe, D., Bowman, L., Pruss, G., Vance, V.B. The amplicon-plus system for high-level expression of transgenes in plants (2002) Nat. Biotech. 20: 622-625.*
Wilde, R.J., Shufflebottom, D., Cooke, S., Jasinska, I., Merryweather, A., Beri, R., Brammer, W.J., Beavan, M., Schuch, W. Control of gene expression in tobacco cells using a bacterial operator-repressor system (1992) EMBO J. 11: 1251-1259.*
Shi, X.M., Miller, H., Verchot, J., Carrington, J.C., Vance, V.B. Mutations in the region encoding the central domain of Helper Component-Proteinase (HC-Pro) eliminate potato virus x/Potyviral synergism (1997) 231: 35-24.*
Gleba, Y., Marillonnet S., Klimyuk, V. Engineering ciral ecpression vectors for plants: the 'full virus' and the 'deconstructed virus' strategies. (2004) 7: 182-188.*
Hull, Mathew's Plant Virology (2002) Academic Press: London, pp. 276-289, 306-308, 392-397.*
Gleba, Y., et al., "Engineering viral expression vectors for plants: the 'full virus' and the 'deconstructed virus' strategies," *Current Opinion in Plant Biology*, 2004, pp. 182-188, vol. 7.
Marillonnet, S., et al., "Systemic *Agrobacterium tumefaciens*-mediated transfection of viral replicons for efficient transient expression in plants," *Nature Biotechnology*, 2005, pp. 718-723, vol. 23(6).
Angell, Susan M. et al., "Consistent gene silencing in transgenic plants expressing a replicating potato virus X RNA", The EMBO Journal, Jan. 29, 1997, pp. 3675-3684, vol. 16, No. 12, Oxford University Press.
Werner, Stefan et al., "High-level recombinant protein expression in transgenic plants by using a double-inducible viral vector", Applied Biological Sciences, Aug. 23, 2011, pp. 14061-14066, vol. 108, No. 34, PNAS.
Drews, Gerhart et al. "Molekulare Pflanzenvirologie", Springer-Verlag, 2004, pp. 89-90 and 137-139.

* cited by examiner

*Primary Examiner* — Russell Kallis
*Assistant Examiner* — Steven Bernacki
(74) *Attorney, Agent, or Firm* — Alston & Bird LLP

(57) ABSTRACT

A process of producing one or more than one protein of interest, comprising: (a) providing a plant or plant cells comprising a first heterologous nucleotide sequence comprising a nucleotide sequence encoding an RNA replicon, and a first inducible promoter operably linked to said nucleotide sequence encoding said RNA replicon; said RNA replicon not encoding a protein providing for cell-to-cell movement of said RNA replicon in said plant; said RNA replicon encoding a polymerase and said one or more than one protein of interest, said polymerase being adapted for replicating said RNA replicon; and (b) inducing, in said plant or plant cells of step (a), said inducible promoter, thereby producing said one or more than one protein of interest in said plant or plant cells.

16 Claims, 16 Drawing Sheets

1: non-infiltrated control
2: test infiltration (alcR; pICH18693)
3. control infiltration (alcR + viral vector; pICH18693 + pICH25408)

PLANT VIRUS-BASED INDUCIBLE EXPRESSION SYSTEM

CROSS-REFERENCE TO RELATED APPLICATIONS

This application is the U.S. National Stage of International Application PCT/EP2007/004688, filed May 25, 2007, which published in English on Dec. 6, 2007 and designates the U.S., and which claims the benefit of EP 06011002.0, filed May 29, 2006 and U.S. Provisional Application No. 60/810,398, filed Jun. 2, 2006; all of which are hereby incorporated herein in their entirety by reference.

FIELD OF THE INVENTION

The present invention relates to a process of producing or expressing one or more than one protein of interest in plants or plant cells using a viral expression system. The invention further relates to plants or plant cells, notably transgenic plants or plants cells, for this process. The invention also provides a process of producing the plants or plant cells of the invention.

BACKGROUND OF THE INVENTION

High yield expression of heterologous proteins in plants can in principle be achieved using viral vectors. However, despite of the existence of different plant viral expression systems, plant viral expression systems are predominantly used for transient expression of a protein of interest in plants following infection (Donson et al., 1991, *Proc Natl Acad Sci U S A*, 88:7204-7208; Chapman, Kavanagh & Baulcombe, 1992, *Plant J*, 2:549-557) or transfection (Marillonnet et al., 2005, *Nat. Biotechnol*, 23:718-723; Santi et al., 2006, *Proc Natl Acad Sci USA*. 103:861-866; WO2005/049839) of a plant host with a recombinant viral vector. Despite of several scientific publications and published patent applications, there are still no established commercial virus-based production systems available that would be easy to scale-up and provide for high yield, predominantly due to the two main reasons:

Firstly, transient plant virus-based expression systems are generally restricted to specific hosts which may not be suitable for large scale cultivation due to their susceptibility to environmental factors. Moreover, they are generally restricted to certain parts of a plant host, thus excluding most of the plant biomass from the production process and as a result minimizes the relative yield of recombinant product per unit of plant biomass down to a level comparable to that achievable using conventional transcription promoters in a transgenic plant;

Secondly, attempts to scale up virus-based production systems by generating transgenic plant hosts having the viral replicon stably integrated in each cell has not provided a solution either, in particular because of underperformance of said replicons in such position and because of steady formation of viral replicons compromises plant growth and development. Usually, systemic viral vectors in transient expression systems can tolerate relatively short (up to one kb) inserts of heterologous nucleic acids, thus being restricted to the expression of relatively small proteins. Viral vectors used for transfection (agrobacterium-mediated delivery, WO2005/049839) can express larger inserts, but require agro-infiltration of whole plants. Obviously, such systems are convenient for the production of many recombinant proteins including antigens, as they require a short time to employ and scale up, but transgenic versions of viral vector-based expression systems could be an advantage in many other applications. Especially, this is an issue for the production of recombinant proteins required in large quantities and at relatively low cost (e.g. different cellulases and other technical enzymes), where transient expression system based on agro-infiltration (WO2005/049839) could not be economically viable. Expression of a viral vector in transgenic plant hosts is usually detrimental for plant growth and development. Also, such expression will eventually lead to transgene silencing. In order to find a solution to this problem, it was attempted to release silenced viral replicon from plant chromosomes with the help of post-transcriptional gene silencing (PTGS) suppressors (U.S. Pat. No. 6,395,962; Mallory et al., 2002, *Nat. Biotechnol*., 20:622-625). A glucocorticoid-inducible expression system based on a plant tripartite RNA virus (Mori et al., 2001, *Plant J.*, 27, 79-86), Brome Mosaic Virus (BMV), gave, perhaps due to PTGS, a very low yield of the protein of interest (3-4 µg/g fresh weight), which is comparable with the yields provided by standard (non-viral) transcriptional promoters.

There is presently no large-scale plant viral expression system the yield and efficiency of which would be sufficiently high to compete on the market with other large-scale expression systems like bacterial, fungal, or insect cell expression systems. Such a plant expression would have to fulfil the following criteria as good as possible:
(i) high yield, including expression of the protein of interest in as many plant tissues as possible and in as many cells of said tissues;
(ii) for preventing a deleterious effect of protein expression on plant cells survival, expression of the protein or product of interest should start in all plant cells of the treated plant or plant tissue at the same time.

Typically, the protein or product of interest accumulates in each cell producing said product or protein up to a certain point. During accumulation, however, degradative processes frequently set on that tend to reduce the yield or quality of the protein or product of interest. Therefore, there is an optimal point in time, where the product or protein of interest should be harvested. This optimal point in time should be reachable in all tissues or cells of a plant and in all plants of a selected lot at the same time in order to make the overall process efficient and profitable.

GENERAL DESCRIPTION OF THE INVENTION

Therefore, it is an object of the invention to provide a process of expressing one or more proteins in a plant system that is easily scalable to large-scale applications, gives a high yield of a protein to be expressed, and, at the same time, is biologically safe in that the probability of uncontrolled expression of recombinant protein of interest is low. It is a further object of the invention to provide an efficient method of producing transgenic plants encoding a viral replicon suitable for expressing a protein of interest from said viral replicon.

Thus, the invention provides a process of producing one or more than one protein of interest, comprising:
(a) providing a plant or plant cells comprising
    a first heterologous nucleotide sequence comprising a nucleotide sequence encoding an RNA replicon, and a first inducible promoter operably linked to said nucleotide sequence encoding said RNA replicon;
    said RNA replicon not encoding a protein providing for cell-to-cell movement of said RNA replicon in said plant;

said RNA replicon encoding a polymerase and said one or more than one protein of interest, said polymerase being adapted for replicating said RNA replicon; and (b) inducing, in said plant or plant cells of step (a), said inducible promoter, thereby producing said one or more than one protein of interest in said plant or plant cells.

The invention further provides a process of producing one or more than one protein of interest, comprising:

(a) providing a plant comprising (i) a first heterologous nucleotide sequence comprising a nucleotide sequence encoding an RNA replicon, and a first inducible promoter operably linked to said nucleotide sequence encoding said RNA replicon;

said RNA replicon not encoding a protein providing for cell-to-cell movement of said RNA replicon in said plant;

said RNA replicon encoding a polymerase and said one or more than one protein of interest, said polymerase being adapted for replicating said RNA replicon; and (ii) a second heterologous nucleotide sequence comprising a sequence encoding a protein enabling cell-to-cell movement of said RNA replicon, wherein said second heterologous nucleotide sequence comprises a second inducible promoter operably linked to said sequence encoding said protein enabling cell-to-cell movement of said RNA replicon; and (b) inducing, in said plant of step (a), said first and said second inducible promoter, thereby producing said one or more than one protein of interest in said plant.

The invention further provides plants or plant cells provided in steps (a) of the above processes. The invention further provides a process of producing a plant or plant cell of the invention, comprising introducing into a plant nuclear chromosome said first heterologous nucleotide sequence and optionally said second heterologous nucleotide sequence, followed by regenerating a transformed plant containing said first and, optionally, said second heterologous nucleotide sequence.

The inventors of the present invention have surprisingly found a process of producing one or more than one protein of interest in plants or plant cells that achieves expression levels that have not been attainable in the prior art. At the same time, the process of the invention is biologically safe and scalable to an industrial level. The exceptional expression levels of the invention are attained by a viral expression system that avoids anti-viral responses by the plant or plant cells such as transgene silencing to an extent hitherto unknown. In the invention, release of the RNA replicon from the nucleotide sequence encoding the RNA replicon and expression of said protein enabling cell-to-cell movement of said RNA replicon are controlled by inducible promoters. Any unintended release of the RNA replicon due to leaky transcription of the RNA replicon from the nucleotide sequence encoding the RNA replicon is confined to those cells in which such leaky transcription has occurred, since said RNA replicon is not capable of cell-to-cell movement in said plant or in said plant cells in the absence of said protein providing for cell-to-cell movement. Importantly, no viral sequences are expressed in the uninduced state at a level capable of triggering transgene silencing. Therefore, transgene silencing is unlikely to occur. Moreover, deleterious effects on the expression yield of the RNA replicon by omitting a protein providing for cell-to-cell movement of said RNA replicon in said plant is compensated by providing a sequence encoding a protein enabling cell-to-cell movement of said RNA replicon in trans to said RNA replicon. Said protein providing for cell-to-cell movement of said RNA replicon is expressed under the control of an inducible promoter. This preserves confinement of a leaky expression of said viral replicon to cells wherein such leaky expression has occurred and avoids gene silencing, but allows high expression levels of said protein of interest in the induced state. Thus, in the invention, the deleterious effects of gene silencing on the yield of a protein of interest are essentially absent.

Further, the inventors have surprisingly found that the transformation efficiency when plant cells are transformed with said first heterologous nucleotide sequence of the invention is higher than in a case where an RNA replicon codes for a protein providing for cell-to-cell movement. In some cases, it was not possible at all to obtain primary transformants with said first heterologous nucleotide sequence, if an RNA replicon coded for a protein providing for cell-to-cell movement. This effect of the invention to improve the transformation efficiency may be due to the incapability of the RNA replicon of the invention for cell-to-cell movement.

In one embodiment of the invention, said plant or plant cells contain a second heterologous nucleotide sequence comprising a nucleotide sequence encoding a protein enabling cell-to-cell movement of said RNA replicon, wherein said second heterologous nucleotide sequence comprises a second inducible promoter operably linked to said nucleotide sequence encoding said protein enabling cell-to-cell movement of said RNA replicon. This embodiment of the invention allows to further increase the yield of production of said one or more than one protein of interest.

In step (a) of the process of producing one or more than one protein of interest, a plant or plant cells are provided with said first heterologous nucleotide sequence. Said plant or plant cells are provided with said first heterologous nucleotide sequence such that a transgenic plant or transgenic plant cells are obtained. In one embodiment, said transgenic plant or said transgenic plant cells contain said first heterologous nucleotide sequence in a nuclear chromosome.

Said plant or plant cells may also be provided with said second heterologous nucleotide sequence such that a transgenic plant or transgenic plant cells are obtained. In one embodiment, said transgenic plant or said transgenic plant cells contain said second heterologous nucleotide sequence in a nuclear chromosome.

Generating transgenic plants containing a heterologous nucleotide sequence stably integrated into a nuclear chromosome or episomally is known in the art. Typically, said heterologous nucleotide sequence will contain a selectable marker gene for selecting of plant cells or plant tissue having integrated said heterologous nucleotide sequence. Whole transgenic plants containing said heterologous nucleotide sequence in cells of said transgenic plant may then be regenerated from transformed cells or tissue using standard procedures in the art of plant biotechnology. Said heterologous nucleotide sequences of the invention are typically DNA.

If plants are to be provided containing said first and said second heterologous nucleotide sequence, said first and said second heterologous nucleotide sequence may be part of one large heterologous nucleotide sequence that is used for transforming plant cells or plants. In this embodiment, said large heterologous nucleotide sequence comprises said first and said second heterologous nucleotide sequence. Alternatively, a first plant containing said first heterologous nucleotide sequence and a second plant containing said second heterologous nucleotide sequence may be generated independently. Said first and said second plant may then be crossed (e.g. by sexual crossing or by cell fusion) to obtain a plant comprising said first and said second heterologous nucleotide sequence. In a further alternative, a transgenic plant or plant cells containing said first heterologous nucleotide sequence may be retransformed with said second heterologous nucleotide sequence for producing plants or plant cells containing said first and said second heterologous nucleotide sequence; or a transgenic plant or plant cells containing said second heterologous nucleotide sequence may be retransformed with said first heterologous nucleotide sequence for producing plants or plant cells containing said second and said first heterologous nucleotide sequence. Herein, "heterologous" means heterologous with respect to said plant.

Said first heterologous nucleotide sequence comprises a nucleotide sequence segment encoding said RNA replicon. Said first heterologous nucleotide sequence further comprises a first inducible promoter operably linked to said nucleotide sequence segment encoding said RNA replicon. Said inducible promoter allows to induce transcription of said nucleotide sequence segment encoding said RNA replicon in step (b) of the process of the invention. Transcription releases said RNA replicon from said nucleotide sequence segment encoding said RNA replicon. Said RNA replicon is a replicon on the RNA level. Said RNA replicon produced in nuclei of plant cells may then migrate into the cytosol where the proteins encoded by said RNA replicon may be produced and where the RNA replicon may be replicated.

Said RNA replicon encodes proteins that may be expressed after said RNA replicon has been released by inducing said inducible promoter. In the present invention, said first RNA replicon encoded by said first heterologous nucleotide sequence is an RNA sequence encoding a polymerase for replicating said RNA sequence, whereby said RNA sequence is adapted to be replicated by the polymerase encoded thereon. Said polymerase thus is an RNA-dependent RNA polymerase that is also referred to herein as "replicase". Said RNA replicon preferably has sequences for translating said polymerase and sequences for binding said polymerase for allowing replication of said RNA replicon in cells of said plant or said plant cells. Said RNA replicon further encodes said one or more than one protein of interest to be expressed as well as sequences required for expressing said one or more proteins of interest such as subgenomic promoters, transcription enhancers or translation enhancers.

In a preferred embodiment, said RNA replicon is derived from an RNA virus, such as a monopartite RNA virus. "Monopartite" means that the monopartite virus has a genome that consists of one nucleic acid molecule. Thus, said RNA replicon of the invention is peferably a monopartite RNA replicon, i.e. it consists of a single type of RNA molecule. In a preferred embodiment, said RNA replicon is derived from a plus-sense single-stranded RNA virus, since such viruses contain the genetic elements required for replication and expression and are optimized by evolution for the purpose of the invention. In said preferred embodiment, said RNA replicon is a plus-sense single-stranded RNA replicon.

"Is derived" means that those genetic elements of RNA viruses required for the invention are used, whereas others may be deleted or rendered dysfunctional. In the invention, a sequence coding for said protein providing for cell-to-cell movement of said virus will be deleted or rendered dysfunctional, e.g. by partial deletion or mutation of sequence portions essential for cell-to-cell movement. Alternatively, a sequence coding for a protein of interest may replace a sequence coding for said protein for cell-to-cell movement fully or partly. "Is derived" implies that sequences of said RNA replicon taken from a plant virus do not have to be identical to corresponding RNA sequence of said RNA virus, but may e.g. have suitably mutations or may exhibit function-conservative differences such as introns inserted in a sequence portion encoding said replicase as described in WO 2005/049839. Since said differences are function-conservative, said sequences preferably code for proteins capable of carrying out replicon functions similarly as they do in said RNA virus from which said RNA replicon is derived. Suitable plus-sense single-stranded RNA viruses from which said RNA replicon of the invention, or the polymerase thereof, may be derived are tobacco mosaic virus (TMV) or potato virus X. Further plant viruses from which said RNA replicon may be derived are given below.

It is, however, also possible to synthesize said RNA replicon, or a cDNA coding therefore, artificially, whereby genetic elements of natural viruses may or may not be used.

Said RNA replicon of the invention does not have to be encoded by one continuous nucleotide sequence segment of said first heterologous nucleotide sequence. Instead, said first heterologous nucleotide sequence may have two or more sequence segments that together encode said RNA replicon. Two or more such sequence segments may be contiguous or may be interrupted by another sequence portion. Formation of said RNA replicon in cells of said plant may then involve site-specific DNA or RNA recombination. In case of DNA recombination, said RNA replicon may be formed via excision of a sequence portion that blocks said RNA replicon from being expressed. Alternatively, one of two or more sequence segments encoding said RNA replicon discontinuously may be flipped by recombination, thereby forming a single continuous sequence segment encoding said RNA replicon. It is also possible that said RNA replicon may be formed by recombination between two replicon precursors, neither of which is an RNA replicon. Such recombination may be ribozyme-mediated trans-splicing as described in WO02/097080.

Said RNA replicon of the invention does not encode a protein providing for cell-to-cell movement of said RNA replicon in said plant. This feature of the invention allows to confine any leaky release of said RNA replicon to the plant cell of said leaky release. A protein providing cell-to-cell movement of said RNA replicon in said plant is generally referred to as "movement protein". Plant viruses usually code for and express one or more proteins for allowing spread of the virus or of genomic RNA of said virus from cell-to-cell. The RNA replicon of the invention must not be able to express a movement protein that would allow said RNA replicon to spread significantly from cell-to-cell in said plant. Said plant or said plant cell should not express a protein providing for cell-to-cell movement of said RNA replicon in said plant, unless under the control of an inducible promoter. In one embodiment, said RNA replicon may contain a part of a movement protein of a natural RNA virus, provided said part of a movement protein does not allow said RNA replicon to spread significantly from cell-to-cell in said plant.

In one embodiment of the process and plant of the invention, said plant comprises a second heterologous nucleotide sequence comprising a nucleotide sequence encoding a protein enabling cell-to-cell movement of said RNA replicon, wherein said second heterologous nucleotide sequence comprises a second inducible promoter operably linked to said nucleotide sequence encoding said protein enabling cell-to-cell movement of said RNA replicon. Said protein may be derived from the same plant RNA virus from which the polymerase of said RNA replicon is derived or from another RNA virus.

Said nucleotide sequence encoding an RNA replicon and said nucleotide sequence encoding a protein enabling cell-to-cell movement are under the control of separate inducible promoters for avoiding that leaky expression from one inducible promoter leads to expression of a movement protein and to formation of said RNA replicon. Thus, said nucleotide sequence encoding an RNA replicon and said nucleotide sequence encoding a protein enabling cell-to-cell movement are present in said plant or plant cells in different expression cassettes. However, these separate inducible promoters need not be different types of inducible promoters. Said separate inducible promoters may be of the same type and may have the same sequence.

Said inducible promoter of said first, said second or any further inducible promoter may be inducible by the same or by different inducing signal or agents. Inducible promoters that can be used in the present invention are given below. In one embodiment, the inducible promoter of said first and/or said second heterologous nucleotide sequences are chemically inducible. In another embodiment, the inducible promoter of said first and/or said second heterologous nucleotide sequences (and optionally of further heterologous nucleotide sequences) are inducible by the same inducing agent such as by IPTG, ethanol, tetracyclin or glucocorticoids.

In step (b) of the process of the invention, said inducible promoter in said plant or plant cells of step (a) is induced, thereby starting expression of said one or more than one protein of interest, thereby producing said one or more than one protein of interest in said plant or plant cells. The mode of induction depends on the type of the inducible promoter. If the inducible promoter is chemically inducible, a chemical agent capable of inducing the promoter is provided to said plant or said plant cells. If different inducible promoters are used for said first and said second heterologous nucleotide sequence, the different chemical agents may be applied concomitantly to said plant or said plant cells, e.g. as a mixture of different inducing agents. If said process is carried out in plant cells in liquid culture, the inducing agents may be added to the culture medium. If said process is carried out in a plant, said inducing agents may be applied to said plant by spraying said plant(s) with a solution or suspension of said inducing agents.

The process of the invention can be used for producing one protein of interest or more than one protein of interest. If one protein of interest is to be produced, a nucleotide sequence coding for said protein of interest may be included in said nucleotide sequence encoding said RNA replicon. In one embodiment, a nucleotide sequence encoding said protein of interest may replace a movement protein gene of a plant RNA virus from which said RNA replicon is derived. Alternatively, it is possible to replace a coat protein gene of an RNA virus from which said RNA replicon is derived by a nucleotide sequence encoding a protein of interest. If two proteins of interest are to be expressed, it is possible to replace (fully or partly) both a movement protein gene and a coat protein gene by a nucleotide sequence encoding a protein of interest.

If two or more proteins of interest are to be produced, said plant or plant cells may comprise a third heterologous nucleotide sequence comprising a nucleotide sequence encoding a further RNA replicon and a third inducible promoter operably linked to said sequence encoding said further RNA replicon. Said further RNA replicon does preferably not encode a protein providing for cell-to-cell movement of said RNA replicon nor of said further RNA replicon in said plant. Said further RNA replicon may then encode one or more further proteins of interest. If said plant encodes two or more RNA replicons, a protein enabling cell-to-cell movement of said RNA replicon may also enable cell-to-cell movement of said further RNA replicon. Alternatively, cell-to-cell movement of said further RNA replicon may be enabled by another protein enabling cell-to-cell movement of said further RNA replicon, expression of which may be under the control of a further inducible promoter.

Said further RNA replicon may be replicable by said polymerase encoded by said RNA replicon encoded by said first heterologous nucleotide sequence. In one embodiment, however, said further RNA replicon encodes a further polymerase for replicating said further RNA replicon, whereby said further polymerase may be different from that of said RNA replicon.

In one embodiment, said RNA replicon and said further RNA replicon are non-competing RNA replicons. Protein production from non-competing RNA replicons or non-competing viral vectors is described in WO 2006/79546 (PCT/EP2006/000721).

Said one or more than one protein of interest may be purified after production in said plant or plant cells from non-desired cell components. Methods or purifying proteins from plants or plant cells are known in the art. In one method, a protein of interest may be directed to the plant apoplast as described in WO 03/020938.

The present invention may in principle be applied to any plants for which infectious RNA viruses exist and for which viral vector systems were established. In one embodiment, dicotyledonous plants are used for practicing the invention. In another embodiment, Solanaceae plants are used. Preferred plants are *Nicotiana* species like *Nicotiana benthamiana* and *Nicotiana tabacum*; preferred plant species other than *Nicotiana* species are *Petunia hybrida, Brassica campestris, B. juncea*, cress, arugula, mustard, Strawberry spinach, *Chenopodium capitatum*, alfalfa, lettuce, sunflower, and cucumber.

The production process of the invention may also be performed in cells of the plants mentioned herein. Said cells by be part of a plant tissue such as leaves or said cells may be present in cell culture such as a suspension culture.

Suitable RNA replicons may be derived from the list of RNA viruses given below. The invention can be applied to monopartite plant RNA viruses. The most preferred plant RNA viruses the invention may be based on are tobamoviruses, notably tobacco mosaic virus, and Potexviruses such as potato virus X. In the case of tobacco mosaic virus, it will generally be the movement protein ORF that is replaced by an ORF of said protein of interest to be expressed. The coat protein ORF may also be removed or replaced by an ORF of a protein of interest.

The major application of the present invention is the production of a protein of interest in plants, plant leaves or plant tissue or cell culture. If the process of the invention is performed in plants, plants that do not enter the human or animal food chain are preferred, like *Nicotiana* species. Plants that do not enter a human or animal food chain can be cultivated in an open field and harvested within certain period after induction of said RNA replicon release, when the expression level of one or more than one protein of interest in plant tissue reaches its peak. Preferably, whole plants or plant parts shall be confined to a closed environment, e.g. a glasshouse or a specially designed chamber for the incubation period necessary to provide for desired level of expression.

The efficiency of the production process of the present invention is such that a new dimension in plant expression systems is attained. The expression levels achievable with the present invention are such that expenditures for downstream processing (including separation and purification of the protein of interest) are low enough to make the process of the invention competitive with other large-scale expression systems. In prior art expression systems using plants stably transformed with viral vectors, the expression level is low, since leakiness of these system allows replicons to be produced even in an uninduced state, thus trigerring mechanisms of PTGS that compromise the yield. Additionally, RNA replicons that are capable of cell-to-cell movement compromize production of stably transformed plant cells carrying said replicons stably incorporated into plant chromosomal DNA. Surprisingly, the inventors found that it is much easier to obtain transgenic plants containing vectors encoding for RNA replicons not capable of cell-to-cell movement, than transgenic plants carrying RNA replicons capable of cell-to cell movement. It is very likely that this phenomenon also contributes to the high expression level in transgenic plants containing viral vectors unable of cell-to-cell movement. The invention provides the first high-yield inducible plant expression system that can be used on a large scale.

Lane 1—control, total soluble protein isolated from untreated plant; lane 2—plants infiltrated with agrobacteria carrying plasmid encoding alcR activator (pICH18693) and treated with 4% ethanol; lane 3—plants infiltrated with mixture of agrobacteria carrying plasmid encoding alcR activator (pICH18693), plasmid encoding viral vector carrying aprotinin gene (pICH25408) and treated with 4% ethanol.

Figure 13:
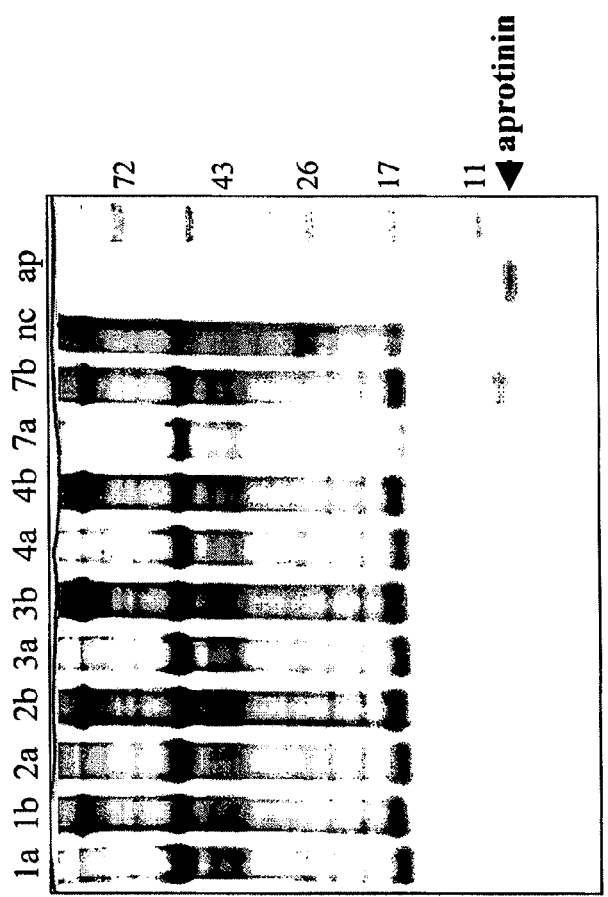

FIG. 13 shows Comassie-stained polyacrylamide gel with results of electrophoretic analysis of total soluble protein extracted from F1 plants obtained from crosses between transgenic plant carrying T-DNA region of plasmid pICH25408 encoding viral vector with aprotinin gene and transgenic plant carrying T-DNA region encoding alcR activator (pICH18693). Plants were treated with 4% ethanol.

DETAILED DESCRIPTION OF THE INVENTION

This invention describes an inducible expression system for high-yield, large-scale production of a protein of interest using RNA replicons that may be derived from monopartite RNA viruses. Said RNA replicons are capable of expressing one or more than one protein of interest in a plant. The process of the invention has biosafety features, provides for tight control of RNA replicon release and prevents said RNA replicon from infecting other plants due to its inability for short distance (cell-to-cell) movement and, optionally, also from long-distance movement.

Figure 1:
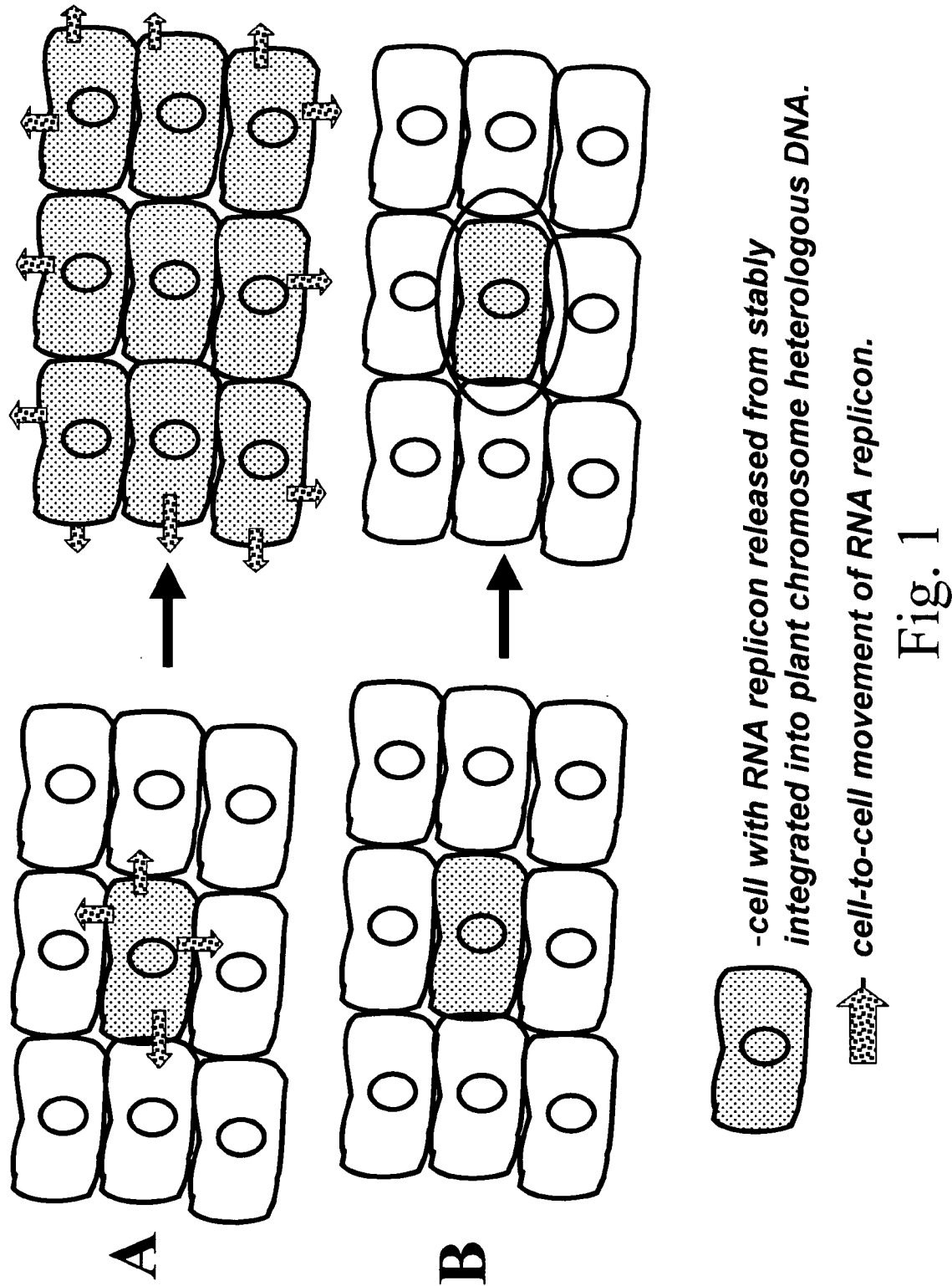
FIG. 1. General principle of the invention. A—spread of RNA replicon capable of cell-to cell movement; B—confinement of the RNA replicon of the invention that is deficient for cell-to-cell movement to the cell where unintended formation of said RNA replicon has occurred.

We have surprisingly found that removal of the cell-to-cell movement function from said RNA viral vectors facilitates selection and regeneration of stably transformed plants encoding said RNA replicon in chromosomal DNA of a plant or plant cells. The basic principle of the invention is shown in FIG. 1. In the case of a viral vector capable of cell-to-cell movement, the leakiness of an inducible system causes viral vector release into the cytosol and further spread to neighboring cells (FIG. 1A). Eventually, this leads to uncontrolled spread of a viral vector within a plant host that compromises growth and development of said plant. In the case of a plant host overcoming such problem and taking control over viral vector replication by mechanism of post-transcriptional gene silencing (PTGS), PTGS would have negative effect on the expression level of a protein of interest in a plant host. In the present invention, leakiness of an inducible system does not have such dramatic effect, since the RNA replicon of the invention is deficient in cell-to-cell movement, whereby PTGS is practically negligible. Said RNA replicon is essentially confined to the cell it was released due to leakiness of the promoter (FIG. 1B), thus improving control over undesired expression of a protein of interest and decreasing potential negative effect of PTGS on productivity of the system.

In the present invention, inducible and tissue-specific promoters can be used to trigger production of a protein of interest in plants or plant cells. Inducible promoters can be divided into two categories according to their induction conditions: those inducible by abiotic factors (temperature, light, chemical substances) and those that can be induced by biotic factors, for example, pathogen or pest attack. Examples of the first category include, but are not limited, heat-inducible (U.S. Pat. No. 05,187,287) and cold-inducible (U.S. Pat. No. 05,847,102) promoters, a copper-inducible system (Mett et al., 1993, *Proc. Natl. Acad. Sci.,* 90, 4567-4571), steroid-inducible systems (Aoyama & Chua, 1997, *Plant J.,* 11, 605-612; McNellis et al., 1998, *Plant J.,* 14, 247-257; U.S. Pat. No. 06,063,985), an ethanol-inducible system (Caddick et al., 1997, *Nature Biotech.,* 16, 177-180; WO09321334; WO0109357; WO02064802), isopropyl beta-D-thiogalactopyranoside (IPTG)-inducible system (Wilde et al., 1992, *EMBO J.,* 11:1251-1259) and a tetracycline-inducible system (Weinmann et al., 1994, *Plant J.,* 5, 559-569). One of the latest developments in the area of chemically inducible systems for plants is a chimaeric promoter that can be switched on by glucocorticoid dexamethasone and switched off by tetracycline (Bohner et al., 1999, *Plant J.,* 19, 87-95). Chemically inducible systems are the most suitable for practicing the present invention. For a review on chemically inducible systems see: Zuo & Chua, (2000, *Current Opin. Biotechnol.,* 11, 146-151) and Moore et al., (2006, *Plant J.,* 45: 651-683). It will be clear for the skilled person that any proteins required for the functionality of the chosen inducible system such as repressors or activators have to be expressed in said plant or said plant cells for rendering the inducible system functional (cf. examples).

Figure 3:
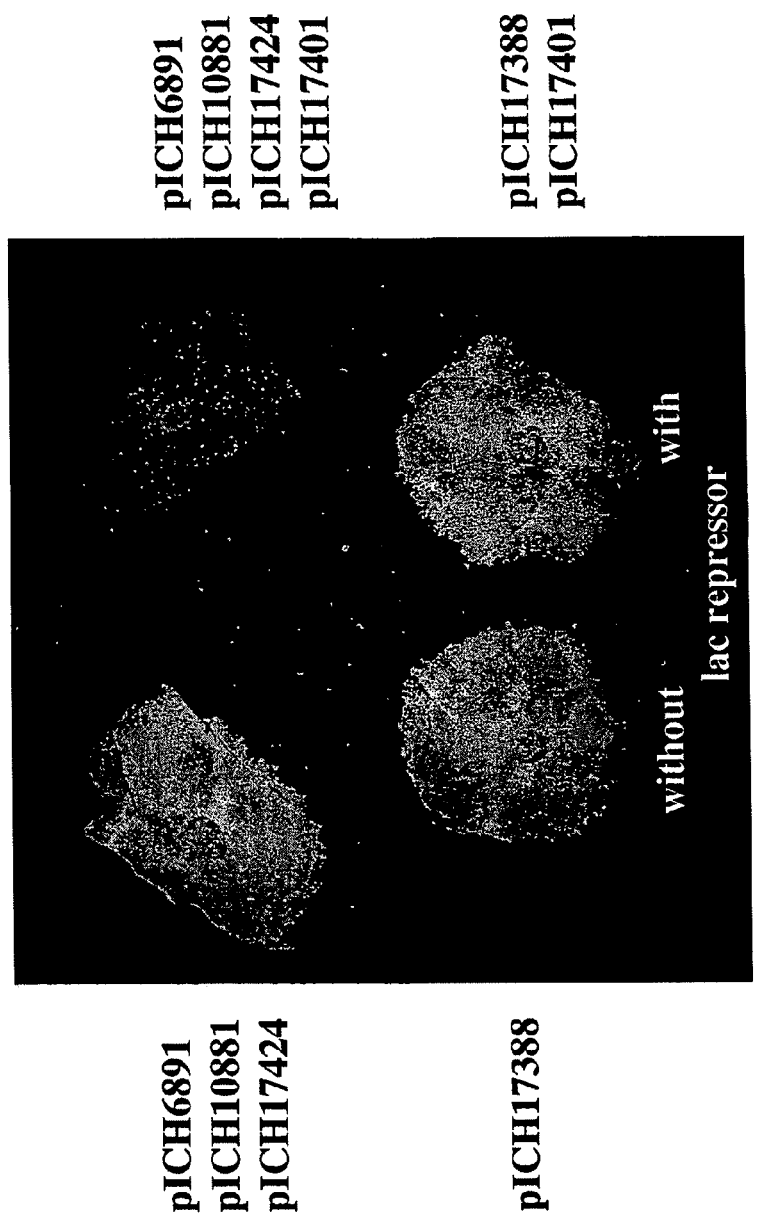
FIG. 3 shows transient expression tests with the inducible lac system. Leaves were infiltrated with different combinations of constructs and 6 days after treatment were monitored under UV light. Light patches before a dark background indicate GFP fluorescence. Left side of the leaf: absence of lac repressor; right side of the leaf: in the presence of the lac repressor. pICH17424 is a 5'-provector with lacO, pICH17388 is the corresponding control construct without lacO. pICH17401 is the lac repressor construct. All samples contain also a GFP 3'-provector and the integrase.

In one embodiment of the invention, we use an IPTG-inducible system for controlling RNA replicon release and production of a protein of interest. The design of exemplary constructs is described in example 1. A bacterial gene encoding the lad repressor was cloned under the control of the strong constitutive 35S promoter. Duplicate lac operator sequences were inserted into the arabidopsis actin2 promoter that drives transcription of the RNA replicon of the invention. This system was tested using a transient expression assay as described in example 2. This system did not show any inhibition of RNA replicon release when a heterologous nucleotide sequence encoding said RNA replicon was infiltrated into a plant together with a construct carrying the lad repressor, possibly because formation of the RNA replicon proceeded the synthesis of the repressor (FIG. 3, right bottom). Indeed, when a provectors system was used that requires a site-specific recombinase for assembly into DNA precursor of the RNA replicon (Marillonnet et al., 2004, *Proc. Natl. Acad. Sci. USA,* 101:6852-6857) in order to delay replicon formation, repression of replicon release was evident (FIG. 3, upper right corner). In the absence of a vector providing for lad repressor (FIG. 3, left top), complete absence of repression of RNA replicon formation in case of provector system was observed.

Figure 4A:
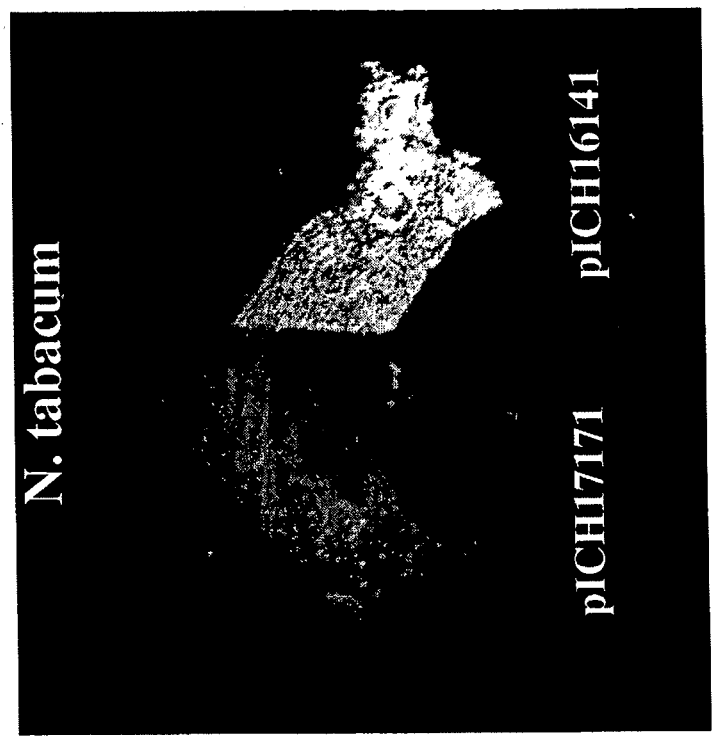
FIG. 4A shows leaves of plants stably transformed with a lac repressor. Plants were agro-infiltrated with vector pICH17171 containing a lacO sequence in its promoter and with the corresponding control construct pICH16141 lacking a lacO sequence.
Figure 4A:
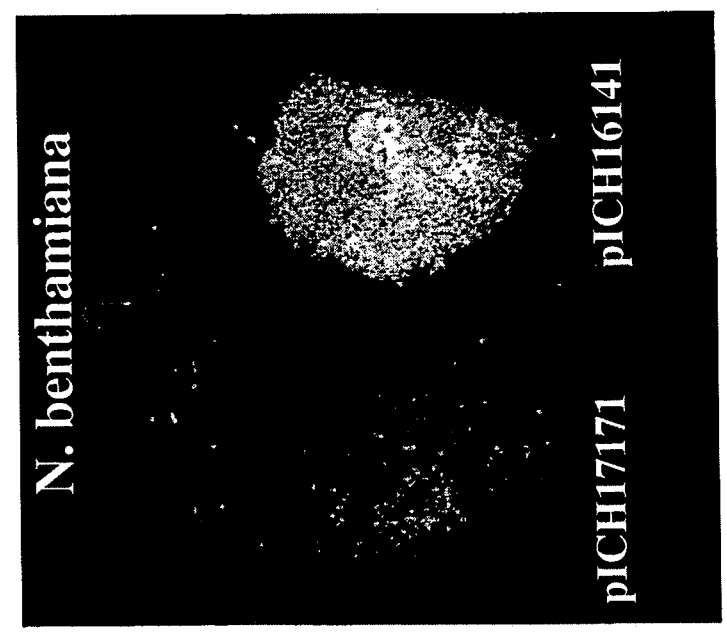
Figure 4B:
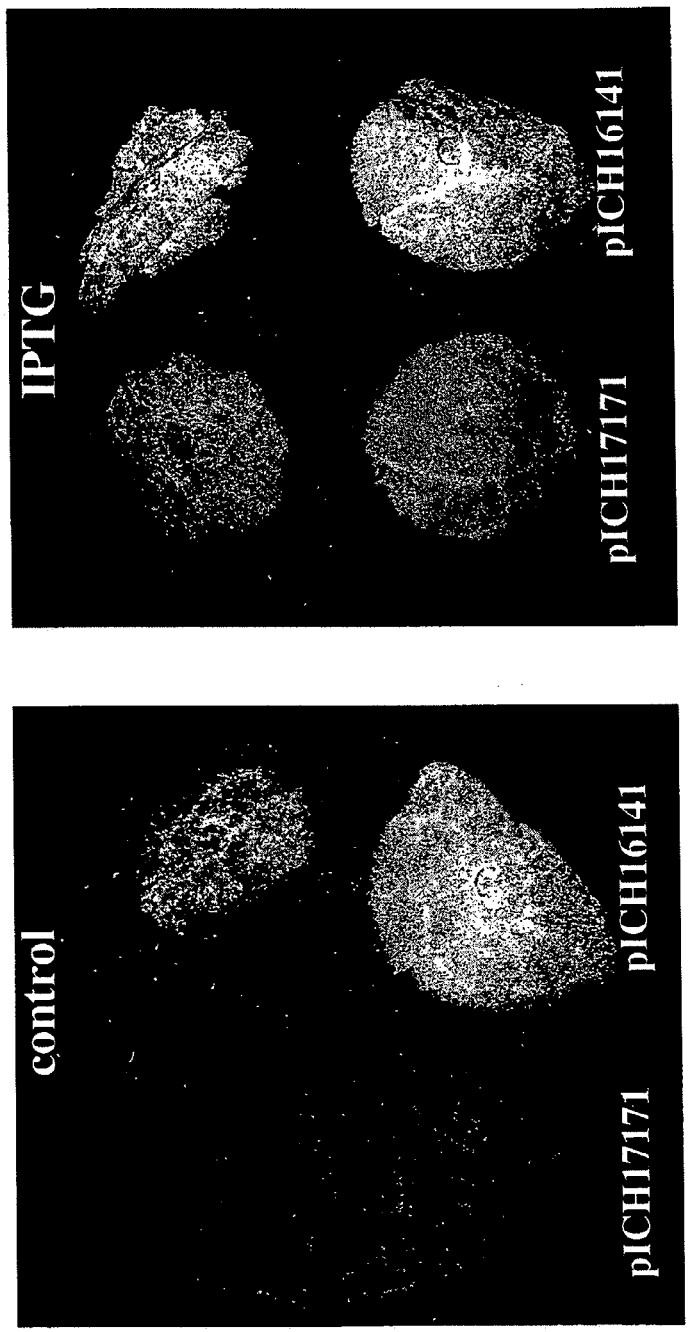
FIG. 4B shows release of repression by treatment with IPTG. N. benthamiana plants stably transformed with a lac repressor were agro-infiltrated with vector pICH17171 containing lacO sequence in its promoter and with the corresponding control construct pICH16141. For induction (right picture), 5 mM IPTG was included in the infiltration buffer. The left picture is in the absence of the inducer IPTG.
Figure 5:
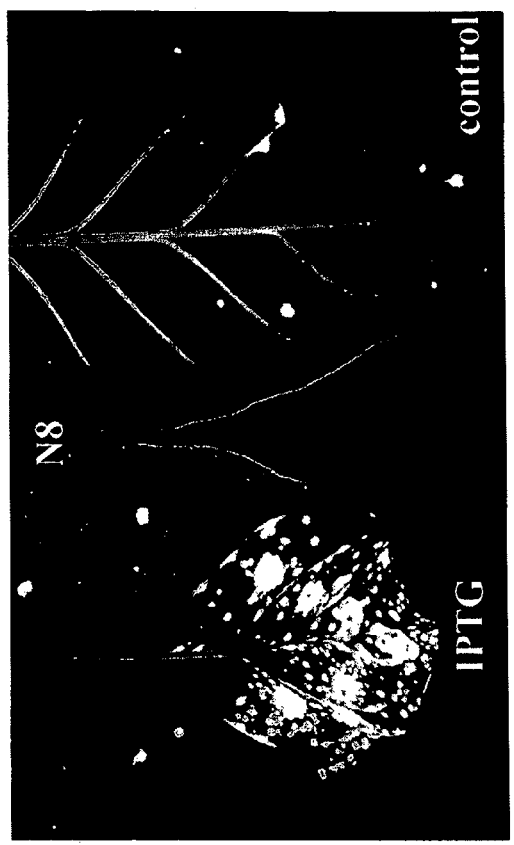
FIG. 5 shows re-transformation of lacI repressor-containing plants (pICH17155 or pICH17401) with constructs providing for RNA replicons. Plants were infiltrated with 5 mM IPTG. Line N6 (left picture) shows high inducibility but also high background, whereas line N8 (right picture) shows low background and low inducibility.
Figure 5:
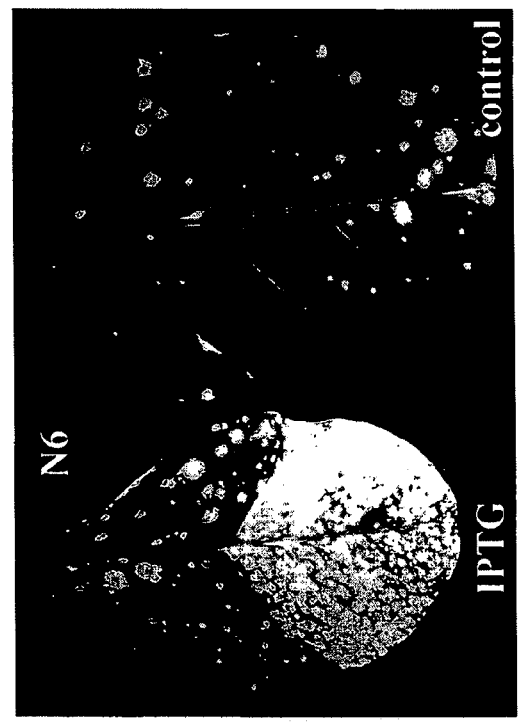

In another embodiment of the invention (example 3), we tested the ability of transgenic plants stably transformed with a construct providing for lacI repressor to repress release of an RNA replicon from a transiently delivered first heterologous nucleotide sequence under control of a promoter with lac operator sequences. It is evident from FIG. 4A that agroinfiltration of construct pICH17171 containing lac operator sequences does not give efficient RNA replicon release in contrast to a control experiment with construct pICH16141 lacking such sequences. Coinfiltration of said transgenic plants with the same constructs and 1 mM IPTG led to the induction of RNA replicon release in case of pICH17171 (FIG. 4B, right panel), while in a control experiment without IPTG, no RNA replicon release was observed (FIG. 4B, left panel). Stable re-transformation of lacI repressor-containing plants with a construct providing for an RNA replicon capable of cell-to-cell movement produced double transformants with severe background expression in the uninduced state (FIG. 5). Summarising the data obtained for LacI/lacO system, it is evident that the best control over RNA replicon release with negligible background expression is obtained in case of an RNA replicon deficient in cell-to-cell movement (pICH17171, FIG. 4A; FIG. 4B, left panel). Constructs containing a functional MP show severe background expression in the uninduced state (pICH17424, FIG. 3, top right; FIG. 5, control). Also, primary transformants with said constructs eventually get silenced for trangene expression, thus becoming useless for high-yield expression of a protein of interest.

Figure 2A:
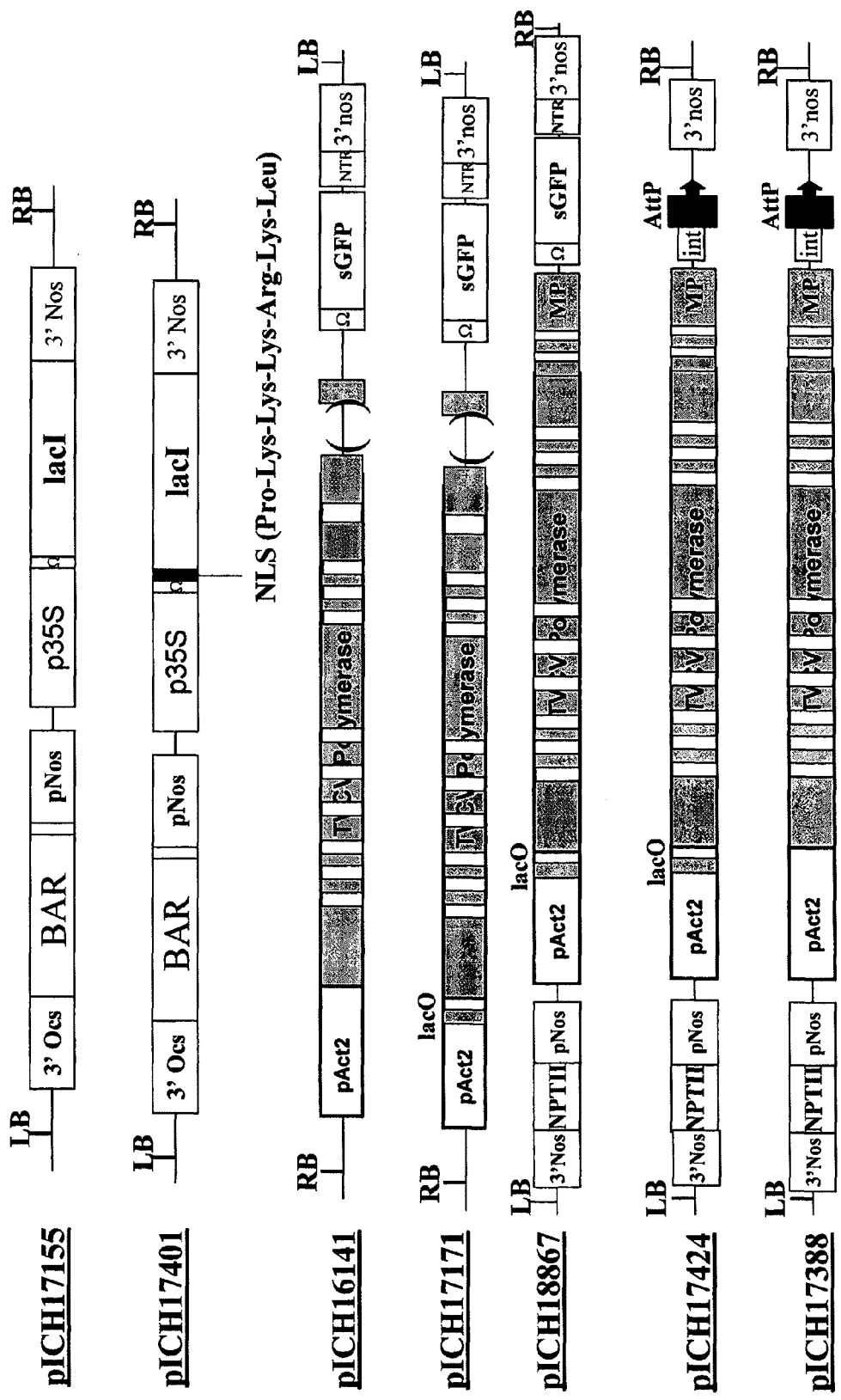
FIG. 2A depicts T-DNA regions of plasmids pICH17155, pICH17401, pICH16141, pICH17171, pICH18867, pICH17424 and pICH17388.
Figure 2B:
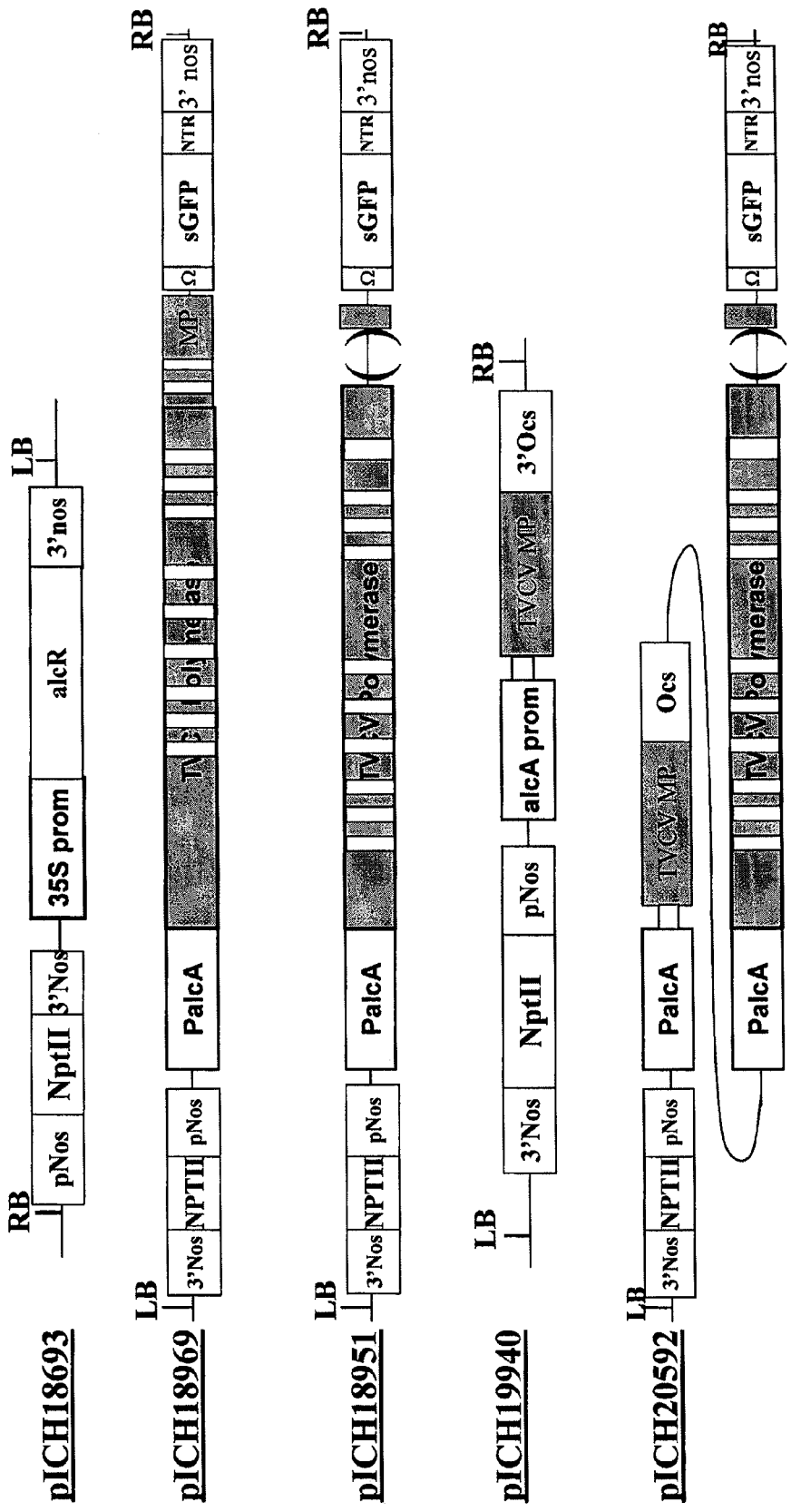
FIG. 2B depicts T-DNA regions of plasmids pICH18693, pICH18969, pICH18951, pICH19940 and pICH20592.
Figure 6:
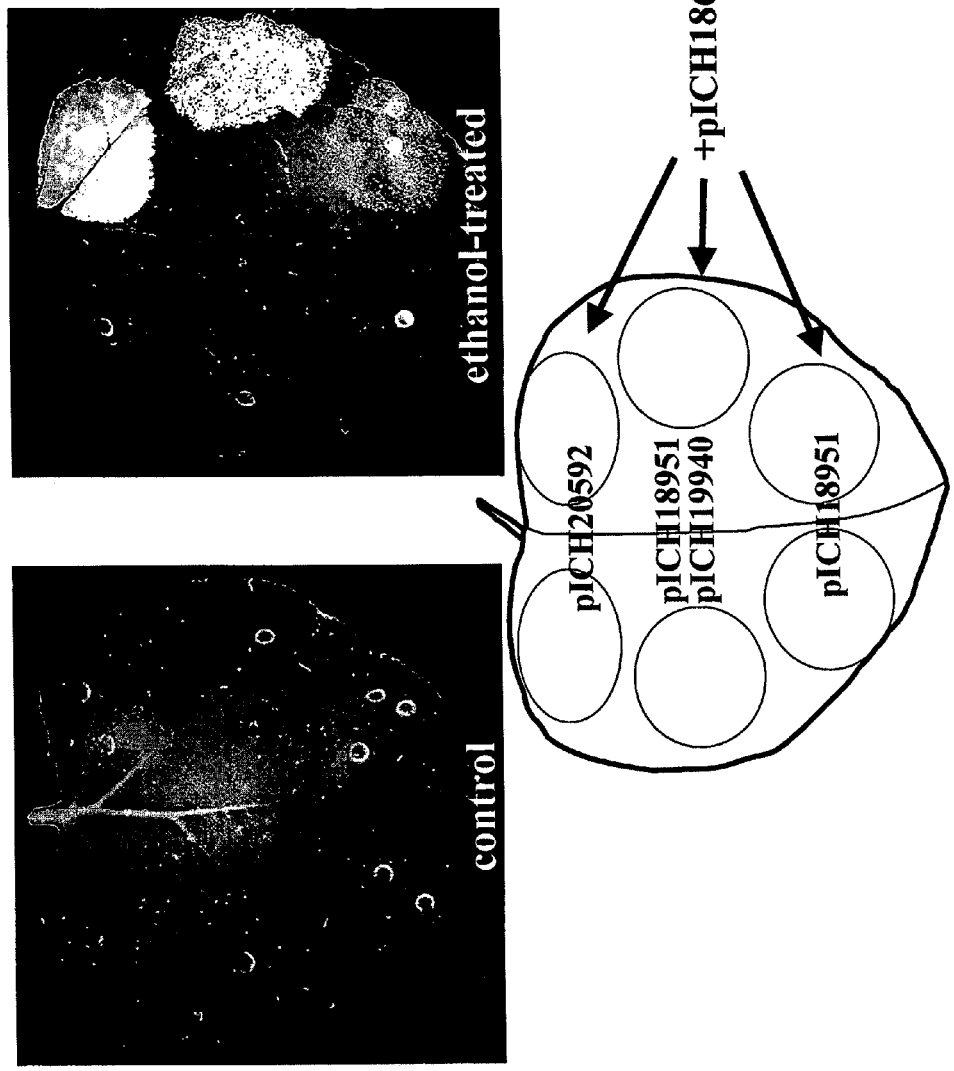
FIG. 6 shows a transient expression test with an ethanol-inducible system based on TMV vector. Control: plants treated 2 days post-infiltration with water; ethanol-treated: plants treated 2 days post-infiltration with 4% ethanol.
Figure 8:
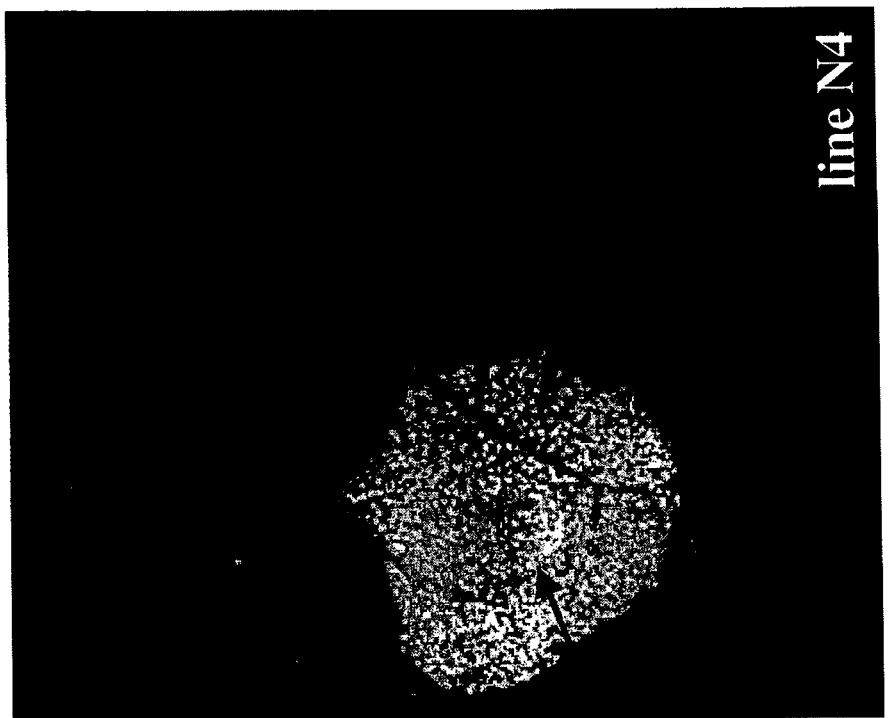
FIG. 8 shows the leaf of a stable transformant carrying the T-DNA of pICH18951 under UV light. The green (light) spot corresponds to the area infiltrated with agrobacteria carrying pICH18693 and sprayed with alcohol.
Figure 9:
FIG. 9 shows transgenic N. benthamiana plant (F1 progeny) expressing GFP after treatment (watering-1% alcohol, and spraying-4% alcohol) with an aqueous alcohol solution.
Figure 10:
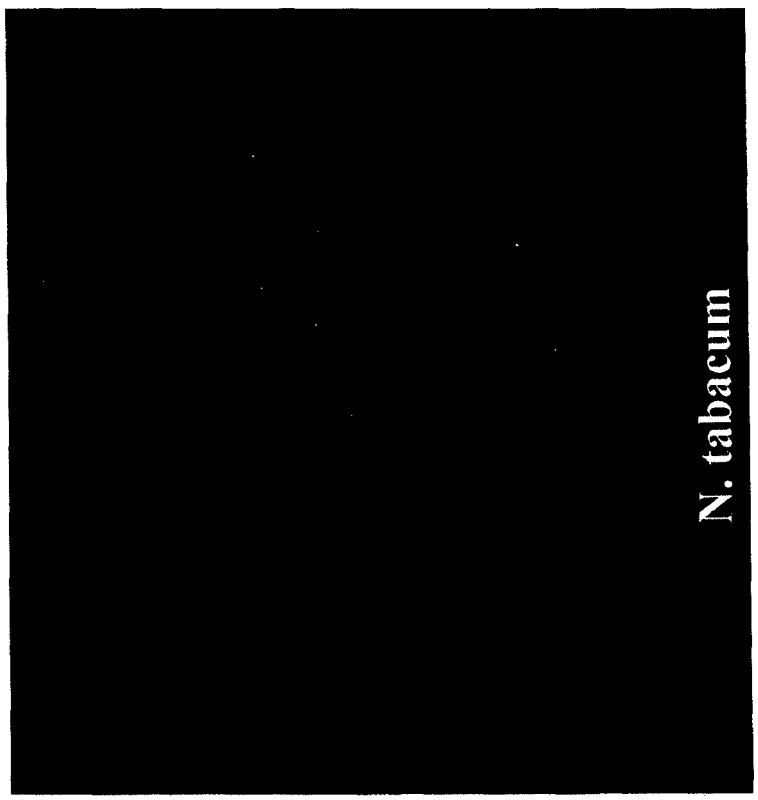
FIG. 10 shows transgenic N. tabacum plant (F1 progeny) expressing GFP after spraying with 4% alcohol solution.
Figure 11:
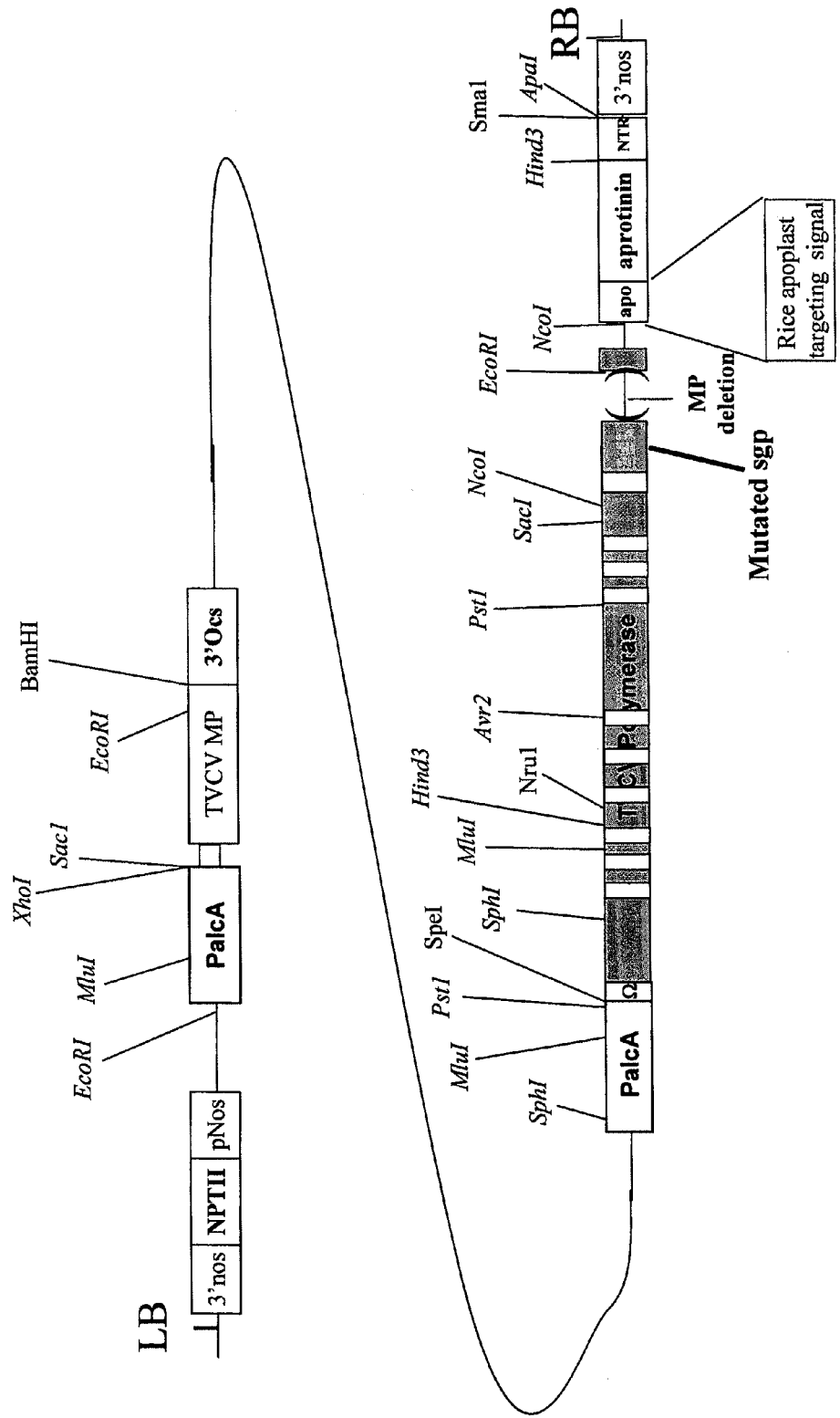
FIG. 11 depicts T-DNA region of plasmid pICH25408. White boxes in the larger grey boxes indicating the TVCV polymerase indicate introns that stabilize transcript in the nucleus and consequently render the transfer of the RNA replicon formed in the cell nucleus to the cytosol. White boxes in the larger grey boxes indicating the TVCV polymerase indicate introns that stabilize transcript in the nucleus and consequently, render the transfer of the RNA replicon formed in the cell nucleus to the cytosol. 3'Nos—transcription termination region of nopaline synthase gene; pNos—promoter of nopaline synthase gene; 3'Ocs—transcription termination region of octopine synthase gene; NPTII—neomycin phosphotransferase II; NTR—tobamoviral non-translated region; PalcA—inducible promoter of inducible A. nidulans alcA gene encoding alcohol dehydrogenase; alcR—transcriptional activator of the alc regulon of Aspergillus nidulans. TVCV MP—turnip veinclearing virus movement protein; sgp—subgenomic promoter.

In another embodiment of the invention, an ethanol-inducible system was used to control RNA replicon release in transgenic plants. The design of constructs is described in example 5 and a schematic presentation of the constructs is shown in FIG. 2B. Results of transient expression experiments of said constructs are shown in FIG. 6. It is evident that the ethanol-inducible system provides for tight control over RNA replicon release, as GFP expression can be observed only in experiments where constructs with alcR activator was coinfiltrated. Practically no background expression was observed in the absence of alcR construct and/or the chemical inducer ethanol (negligible expression was observed in the presence of alcR construct). Agroinfiltration of N. benthamiana plants transgenic for constructs providing for an RNA replicon (pICH18951) with alcR constructs in the presence of 4% ethanol showed RNA replicon formation reported by strong GFP expression (FIG. 8). Surprisingly, in the ethanol-inducible system no primary transformants (not even with leakiness of control over RNA replicon release) were obtained with viral constructs containing a functional MP (Example 5). This can be explained by the leakiness of the system in plant callus/cell culture (Roberts et al., 2005, *Plant Physiol.*, 138:1259-1267) due to cell-to cell movement of the RNA replicon. This explanation is supported by the surprising finding that primary transformants providing for RNA replicons under control of the ethanol-inducible promoter could be generated with no difficulties, if the RNA replicon does not encode a protein for cell-to-cell movement in the plant host used. We also demonstrated that cross-progeny of transgenic plants with a vector providing for an RNA replicon and alcR-containing transgenics reveal strong ubiquitous expression of GFP after treatment with ethanol (FIGS. 9 and 10). In another embodiment of this invention, we demonstrate that our system works efficiently with proteins other than reporter genes, like GFP. A construct for expression of aprotinin is shown in FIG. 11. Analysis of recombinant aprotinin production in F1 progeny of *N. benthamiana* plants after treatment with alcohol demonstrated a high expression level detectable on Coomassie-stained gel as one of major protein bands.

In the examples, we use TMV-based RNA replicons. However, many different viruses belonging to different taxonomic groups can be used for the construction of RNA virus-based vectors according to the present invention. Names of orders, families and genera are in italic script, if they are approved by the ICTV. Taxa names in quotes (and not in italic script) indicate that this taxon does not have an ICTV international approved name. Species (vernacular) names are given in regular script. Viruses with no formal assignment to genus or family are indicated):

RNA Viruses:

ssRNA Viruses: Family: Bromoviridae, Genus: Alfamovirus, Type species: alfalfa mosaic virus, Genus: Ilarvirus, Type species: tobacco streak virus, Genus: Bromovirus, Type species: brome mosaic virus, Genus: Cucumovirus, Type species: cucumber mosaic virus;

Family: Closteroviridae, Genus: Closterovirus, Type species: beet yellows virus, Genus: Crinivirus, Type species: Lettuce infectious yellows virus, Family: Comoviridae, Genus: Comovirus, Type species: cowpea mosaic virus, Genus: Fabavirus, Type species: broad bean wilt virus 1, Genus: Nepovirus, Type species: tobacco ringspot virus;

Family: Potyviridae, Genus: Potyvirus, Type species: potato virus Y, Genus: Rymovirus, Type species: ryegrass mosaic virus, Genus: Bymovirus, Type species: barley yellow mosaic virus;

Family: Sequiviridae, Genus: Sequivirus, Type species: parsnip yellow fleck virus, Genus: Waikavirus, Type species: rice tungro spherical virus; Family: Tombusviridae, Genus: Carmovirus, Type species: carnation mottle virus, Genus: Dianthovirus, Type species: carnation ringspot virus, Genus: Machlomovirus, Type species: maize chlorotic mottle virus, Genus: Necrovirus, Type species: tobacco necrosis virus, Genus: Tombusvirus, Type species: tomato bushy stunt virus, Unassigned Genera of ssRNA viruses, Genus: Capillovirus, Type species: apple stem grooving virus;

Genus: Carlavirus, Type species: carnation latent virus; Genus: Enamovirus, Type species: pea enation mosaic virus, Genus: Furovirus, Type species: soil-borne wheat mosaic virus, Genus: Hordeivirus, Type species: barley stripe mosaic virus, Genus: Idaeovirus, Type species: raspberry bushy dwarf virus;

Genus: Luteovirus, Type species: barley yellow dwarf virus; Genus: Marafivirus, Type species: maize rayado fino virus; Genus: Potexvirus, Type species: potato virus X; Genus: Sobemovirus, Type species: Southern bean mosaic virus, Genus: Tenuivirus, Type species: rice stripe virus, Genus: Tobamovirus, Type species: tobacco mosaic virus, Genus: Tobravirus, Type species: tobacco rattle virus, Genus: Trichovirus, Type species: apple chlorotic leaf spot virus; Genus: Tymovirus, Type species: turnip yellow mosaic virus; Genus: Umbravirus, Type species: carrot mottle virus; Negative ssRNA Viruses: Order: Mononegavirales, Family: Rhabdoviridae, Genus: Cytorhabdovirus, Type Species: lettuce necrotic yellows virus, Genus: Nucleorhabdovirus, Type species: potato yellow dwarf virus;

Negative ssRNA Viruses: Family: Bunyaviridae, Genus: Tospovirus, Type species: tomato spotted wilt virus;

dsRNA Viruses: Family: Partitiviridae, Genus: Alphacryptovirus, Type species: white clover cryptic virus 1, Genus: Betacryptovirus, Type species: white clover cryptic virus 2, Family: Reoviridae, Genus: Fijivirus, Type species: Fiji disease virus, Genus: Phytoreovirus, Type species: wound tumor virus, Genus: Oryzavirus, Type species: rice ragged stunt virus;

Unassigned Viruses: Genome ssDNA: Species: banana bunchy top virus, Species: coconut foliar decay virus, Species: subterranean clover stunt virus, Genome: dsDNA, Species: cucumber vein yellowing virus; Genome: dsRNA, Species: tobacco stunt virus, Genome: ssRNA, Species Garlic viruses A,B,C,D, Species grapevine fleck virus, Species maize white line mosaic virus, Species olive latent virus 2, Species: ourmia melon virus, Species Pelargonium zonate spot virus;

Satellites and Viroids: Satellites: ssRNA Satellite Viruses: Subgroup 2 Satellite Viruses, Type species: tobacco necrosis satellite, Satellite RNA, Subgroup 2 B Type mRNA Satellites, Subgroup 3C Type linear RNA Satellites, Subgroup 4 D Type circular RNA Satellites, Viroids, Type species: potato spindle tuber viroid.

Different RNA viruses have one or more viral proteins for cell-to-cell or short distance movement. For example, in the case of TMV, one protein (MP) is required; the tripartite Brome Mosaic Virus (BMV) requires two proteins—3a and CP. The monopartite RNA virus potato virus X (PVX) has four proteins responsible for cell-to-cell movement: proteins encoded by triple gene block (TGB) and coat protein (CP). However, a deficiency in one of two or more proteins required for cell-to-cell movement is enough to block efficient short distance movement of a viral vector. For more details about plant viral movement proteins, see the recent review of WJ Lucas (2006, *Virology*, 344:169-184).

In the present invention, said first heterologous nucleotide sequence has a sequence segment encoding said RNA replicon. Alternatively, said first heterologous nucleotide sequence may have more than one sequence segments that code together for said RNA replicon, i.e. said RNA replicon is not encoded by one continuous DNA. Instead, said RNA replicon is encoded discontinuously by two or more sequence segments, whereby said segments may be present contiguous to each other. Formation of said RNA replicon may then require rearrangement of said segments, e.g. by recombination. A recombinase for said recombination may be provided by an engineered plant host, thus confining the inducible expression of said viral replicon to a plant host capable of expressing said recombinase. As an example, a sequence segment may code for a part of said polymerase of said RNA replicon, and another sequence segment coding for another part of said polymerase may be present in said first heterologous nucleotide sequence in a flipped orientation relative to the first sequence segment. The flipped part may be flanked by recombination sites (see WO2004/108934). In this situation, the transcript of the first heterologous nucleotide sequence or a sequence segment thereof will not be an RNA replicon, since no functional polymerase can be translated from the transcript. Providing a site-specific recombinase recognizing the recombination sites allows to flip one of said segments such that a replicon is encoded continuously. In this embodiment, providing the recombinase may function as a switch for switching on RNA replicon formation and expression of a sequence of interest in the induced state and contributes to a high biological safety. Preferably, said recombinase is under control of an inducible promoter. If a recombinase is used for switching on the process of the invention, said recombinase may be provided to said plant or plant leaves transiently, whereby said providing may act as a switch for expressing said one or more than one protein of interest. Preferably, such a recombinase may be stably encoded in plant cells, and expressing of the recombinase under control of a constitutive or inducible promoter. Inducing recombinase expression by inducing said promoter may then cause expression of said sequence of interest. In one embodiment, the recombinase will be encoded by said first heterologous nucleotide sequence and expression of the recombinase will be under the control of the inducible promoter of said first heterologous nucleotide sequence.

Alternatively, both segments may be present on different T-DNAs stably incorporated in different plant chromosomes. Formation of an RNA replicon will then require transcription of both segments and trans-splicing of both transcripts for assembling said RNA replicon. This embodiment may be used for quickly segregating the segments that encode together said RNA replicon in progeny plants or cells as described in WO02/097080, thus contributing to the biological safety of the system.

In the examples, we describe transgenic plants encoding one type of RNA replicon derived from a plant virus. However, in the process of the invention, two or more different RNA replicons (notably two or more different monopartite RNA replicons) may be used in a transgenic plant or plant cells, whereby such different RNA replicons are preferably derived from different plant viruses. Such different plant viruses from which said different RNA replicons may be derived are preferably synergistic or non-competing viruses. "Synergistic" and "non-competing" are used herein synonymously. Synergistic viruses can coexist and efficiently amplify in the same plant cells. Similarly, RNA replicons derived from synergistic RNA viruses can co-exist and efficiently amplify in the same plant cells. An example of such a synergistic pair of RNA replicons is a pair of RNA replicons, whereby one RNA replicon is derived from TMV and the other RNA replicon is derived from PVX. Such synergistic RNA replicons can be released from different expression cassettes utilising the same or different inducible promoters. Synergistic RNA replicons may be used for the expression of two or more proteins or protein subunits of interest, such as the heavy and the light chain of a monoclonal antibody, in the same plant cell. Processes of expressing two or more proteins of interest in the same plant or in the same plant cells using different (non-competing) viral vectors is described in WO 2006/79546 (PCT/EP2006/000721) which is incorporated herein by reference in its entirety.

In the examples, we predominantly used *Agrobacterium*-mediated T-DNA delivery in plant cells, whereby said T-DNA contains said first and/or said second heterologous nucleotide sequence. Various methods may be used for the delivery of vectors into plant cells such as direct introduction of a heterologous nucleotide sequence into cells by means of microprojectile bombardment, electroporation or PEG-mediated transformation of protoplasts. *Agrobacterium*-mediated plant transformation is preferred. Thus, a heterologous nucleotide sequence may be transformed into plant cells by various technologies such as by a Ti-plasmid vector carried by *Agrobacterium* (U.S. Pat. No. 5,591,616; U.S. Pat. No. 4,940,838; U.S. Pat. No. 5,464,763), particle or microprojectile bombardment (U.S. Pat. No. 05,100,792; EP 00444882B1; EP 00434616B1). In principle, other plant transformation methods can also be used e.g. microinjection (WO 09209696; WO 09400583A1; EP 175966B1), electroporation (EP00564595B1; EP00290395B1; WO 08706614A1), etc. The choice of the transformation method depends inter alia on the plant species to be transformed. For example, microprojectile bombardment may be preferred for monocot transformation, while for dicots, *Agrobacterium*-mediated transformation gives generally better results.

The present invention is preferably carried out with higher, multi-cellular plants. Preferred plants for the use in this invention include any plant species with preference given to agronomically and horticulturally important species. Common crop plants for the use in the present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. Plant species preferred for practicing this invention include but not restricted to:

Representatives of Graminae, Compositae, Solanacea and Rosaceae. Additionally, preferred species for use in the invention, as well as those specified above, plants from the genera: *Arabidopsis, Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea,* and the Olyreae, the Pharoideae and many others.

In one embodiment of the invention, RNA replicons derived from TMV are used with *Nicotiana* plants. In another embodiment, RNA replicons derived from PVX are used with *Nicotiana* plants.

Proteins of interest, or fragments thereof, that can be expressed, in sense or antisense orientation, using the invention include: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* glgA protein, MAPK4 and orthologues, nitrogen assimilation/methanolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CryIC toxin, delta endotoxin, polyopeptide toxin, protoxin etc.), insect specific toxin AaIT, cellulose degrading enzymes, E1 cellulase from *Acidothermus celluloticus*, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, Umbellularia californica C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, 6-desaturase, protein having an enzymatic activity in the peroxysomal-oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, ribozyme, protein having posttranslational cleavage site, protein fusion consisting of a DNA-binding domain of Gal4 transcriptional activator and a transcriptional activation domain, a translational fusion of oleosin protein with protein of interest capable of targeting the fusion protein into the lipid phase, DHPS gene conferring sulfonamide resistance, bacterial nitrilase, 2,4-D monooxygenase, acetolactate synthase or acetohydroxyacid synthase (ALS, AHAS), polygalacturonase, bacterial nitrilase, fusion of amino terminal hydrophobic region of a mature phosphate translocator protein residing in the inner envelope membrane of the plastid with protein of interest to be targeted into said membrane etc.

Any human or animal protein can be expressed using the system of the invention. Examples of such proteins of interest include inter alia the following proteins (pharmaceutical proteins): immune response proteins (monoclonal antibodies, single chain antibodies, T cell receptors etc.), antigens, colony stimulating factors, relaxins, polypeptide hormones, cytokines and their receptors, interferons, growth factors and coagulation factors, enzymatically active lysosomal enzyme, fibrinolytic polypeptides, blood clotting factors, trypsinogen, 1-antitrypsin (AAT), as well as function-conservative proteins like fusions, mutant versions and synthetic derivatives of the above proteins.

The disclosures of European patent application No. 06 011 002 filed on May 29, 2006 and of U.S. provisional patent application 60/810,398 filed on Jun. 2, 2006, the priorities of which are claimed by the present patent application, are incorporated herein by reference in their entireties.

EXAMPLES

Example 1

IPTG-Inducible lac-System

Constructs Design

The lac repressor (lacI, Acc. J01636) was amplified by PCR using primers laclpr1 (SEQ ID NO: 1) (5'-gat cca tgg aac cag taa cgt tat ac-3') and laclpr2 (SEQ ID NO: 2) (5'-tc tgg atc ctc act gcc cgc mt cca gtc g-3') and cloned as NcoI-BamHI fragment into standard binary vector pICBV1 giving construct pICH17155 (FIG. 2A). A nuclear localization signal (NLS) was introduced to the N-terminus by using primer laclpr5 (SEQ ID NO: 3) (5'-cgc cat ggg ccc taa gaa gaa gag gaa ggt tga acc agt aac gtt ata cga tgt c-3') instead of laclpr1 giving construct pICH17401 (FIG. 2A). This construct was stably transformed into *Nicotiana tabacum* and *N. benthamiana* plants using standard transformation techniques (Horsh et al., 1985, *Science*, 227, 1229-1231).

A synthetic lac operator sequence (SEQ ID NO: 4) (aat tgt gag cgc tca caa tt) was introduced between the TATA-box and the transcriptional start of the actin2-promoter (An et al., 1996, *Plant J.*, 10: 107-121) of several viral vectors. This was done by combining two overlapping PCR-products made with primers A: brb4nosph (SEQ ID NO: 5) (5'-gga acc ctg tgg ttg gca cat-3') and lacOact2pr2 (SEQ ID NO: 6) (5'-cga att gtg agc gct cac aat tta tat agg cgg gtt tat ctc-3') and primers B: lacoactprl (SEQ ID NO: 7) (5'-taa att gtg agc gct cac aat tcg ctt tga agt ttt agt ttt att g-3') and rdrppr4 (SEQ ID NO: 8) (5'-ttt ctgcag gaa atg aaa ggc cgc gaa aca ag-3'). The resulting product was cloned as KpnI-SphI fragment into viral vector pICH16141 resulting in vector pICH17171. Additional viral vectors were derived from pICH17171 by subcloning the promoter using convenient restriction enzymes. These vectors were optimized for expression (Marillonnet et al., 2005, *Nat Biotechnol*, 23:718-723) and contain either full MP (pICH18867) or a deletion of MP (pICH17171). Additionally, a 5'-provector (Marillonnet et al., 2004, Proc Natl Acad Sci USA, 101:6852-6857) was constructed (pICH17424) that proved to be useful for transient tests (see Example 2).

Example 2

Test of Repression Efficiency in a Transient System

Transient expression experiments were carried out using a mixture of agrobacterial strains harbouring different constructs under test. We could not see any repression in transient assays while using fully assembled viral vectors. Most likely, the construct was already transcribed into the viral RNA replicon prior to translation of the repressor. Thus, we used viral provectors pICH17424 (FIG. 2A) and pICH6892 (Marillonnet et al., 2004, *Proc Natl Acad Sci USA*, 101:6852-6857) that are assembled in planta into DNA precursor of viral RNA replicon by the activity of a site-specific recombinase (Marillonnet et al., 2004, *Proc Natl Acad Sci USA*, 101:6852-6857). This additional step should delay assembly of viral vector and provide enough time for the repressor to be translated and bound to the operator sequence in the viral construct. Indeed, we could see strong repression of viral amplification using this approach (FIG. 3).

Example 3

LacI Repressor Activity in Stably Transformed Plants and Induction by IPTG

The repressor construct pICH17401 (FIG. 2A) was stably transformed in *N. tabacum* and *N. benthamiana* plants using standard transformation techniques (Horsh et al., 1985, *Science*, 227, 1229-1231). Repressor-activity was demonstrated by agroinfiltration of transformed plants with lacO-containing viral constructs (FIG. 4A). Inducibility was tested similarly by agroinfiltration with the same constructs and including IPTG in the infiltration buffer (FIG. 4B).

Example 4

Retransformation of Repressor-Containing Plants with Viral Constructs

*N. tabacum* plants carrying the lacI-repressor recombinant DNA (pICH17401, FIG. 2A) stably integrated in their genome were transformed a second time with a full viral vector construct containing the lac operator (pICH18867, FIG. 2A). Several plants could be regenerated, but all of them showed more or less severe background expression of the viral vector.

Infiltration of IPTG (5 mM) into the leaves of double transformants could actually induce RNA replicon amplification in some of the transgenic plants (FIG. 5). However, we found that all primary transformants with leaky expression of RNA replicon were eventually subject to transgene silencing and produced progeny that did not show any release of RNA replicon under inducing conditions.

Example 5

Design of Constructs for Ethanol-Inducible System

The principle of the ethanol-inducible system was described by Caddick and colleagues (1998, *Nat Biotechnol*, 16:177-180). The transcriptional activator alcR under the control of the CaMV 35S promoter (construct pICH18693, FIG. 2B) was designed as described by Caddick and colleagues (1998, *Nat Biotechnol*, 16:177-180). This construct was stably transformed into *N. tabacum* and *N. benthamiana* plants (Horsh et al., 1985, *Science*, 227, 1229-1231). The alcA promoter was amplified by PCR using primers alcApr1 (SEQ ID NO: 9) (5'-cat gaa ttc tag gat tgg atg cat gcg g-3') and alcApr2 (SEQ ID NO: 10) (5'-cag ctc gag gtc gtc ctc tcc aaa tga aat g-3') and fused as EcoRI-XhoI fragment to TMV-based viral vectors with (pICH18969, FIG. 2B) or without (pICH18951, FIG. 2B) functional MP and separately to the functional viral MP (pICH19940, FIG. 2B). Additionally, constructs pICH18951 and pICH19940 were combined into one vector (pICH20592, FIG. 2B). All these constructs, except pICH18969, were transformed both into *N. tabacum* and *N. benthamiana* using standard transformation techniques. It was not possible to obtain primary transformants with constructs encoding an RNA replicon with a functional MP.

Figure 2C:
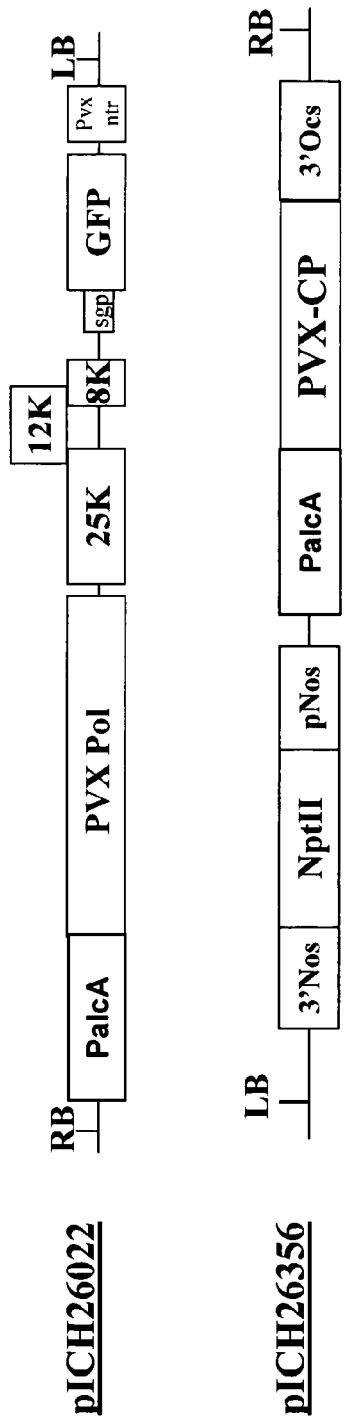
FIG. 2C depicts T-DNA regions of plasmids pICH26022 and pICH26356. White boxes in the larger grey boxes indicating the TVCV polymerase indicate introns that stabilize transcript in the nucleus and, consequently, render the transfer of the RNA replicon formed in the cell nucleus to the cytosol more efficient. 3'Nos—transcription termination region of nopaline synthase gene; pNos—promoter of nopaline synthase gene; p35S-35S promoter of CaMV; pAct2—promoter of A. thaliana actin 2 gene; NLS—nuclear localization signal; lacO—operator sequence of E. coli lac operon; lacI—repressor gene of E. coli lac operon; BAR—gene conferring resistance to herbicide phosphinothricin; int—5' part of intron sequence; AttP—recombination site recognized by integrase phC31. NPTII—neomycin phosphotransferase II; sGFP—synthetic green fluorescent protein; NTR—tobamoviral non-translated region; PalcA—inducible promoter of inducible A. nidulans alcA gene encoding alcohol dehydrogenase; alcR—transcriptional activator of the alc regulon of Aspergillus nidulans. TVCV MP—turnip vein clearing virus movement protein; PVX CP—potato virus X coat protein; PVX Pol—potato virus X RNA-dependent RNA polymerase; 25K, 12K, 8K—triple gene block; sgp—subgenomic promoter.

The alcA promoter was also amplified using primers alcApr4 (SEQ ID NO: 11) (5'-cgc gca tgc tac tag gat tgg ata cat gcg gaa c-3') and alcApr5 (SEQ ID NO: 12) (5'-ttt ggt ctc atc aac tcc aaa tga aat gaa ctt cc-3') and cloned as SphI-BsaI fragment into the PVX-based viral vector pICH25233 replacing $^{35}$S promoter and giving construct pICH26022 (FIG. 2C). Fusion of alcA promoter to the PVX coat protein involved in cell-to-cell movement (pICH26356, FIG. 2C) was done by cloning of an EcoRI-SacI fragment from pICH19940 into pICH22066.

Example 6

Transient Expression of TMV-Constructs Induced by Ethanol

The constructs mentioned above were tested by agroinfiltration in *N. benthamiana* plants (FIG. 6). Plants were treated at 2 days post-infiltration either with a 4% ethanol solution or with water as control. Amplification of the viral vector and expression of GFP was only induced in the ethanol-treated plants and only in the presence of the activator alcR. Very weak background expression was observed in control plants in the presence of alcR.

Example 7

Transient Expression of PVX-Constructs Induced by Ethanol

Figure 7:
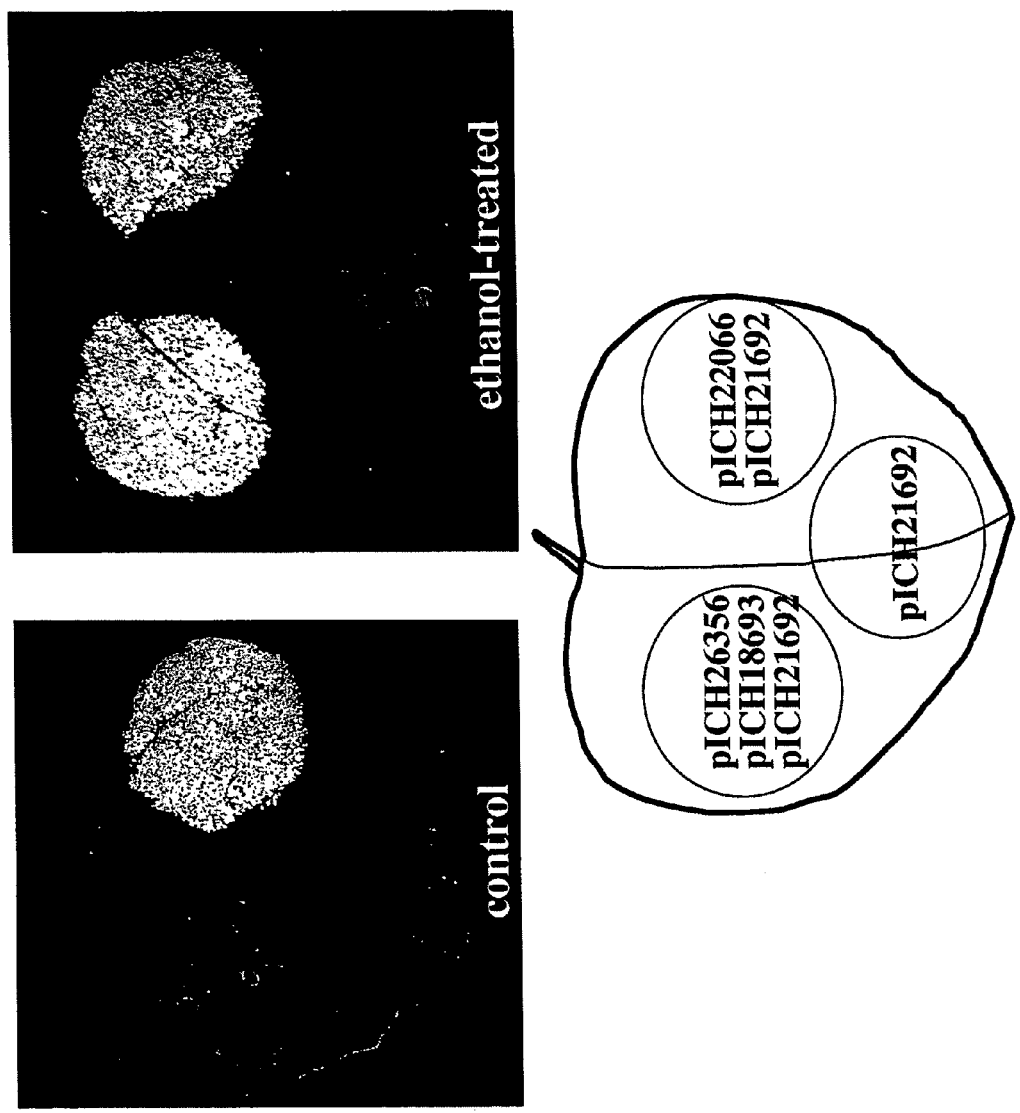
FIG. 7 shows a transient expression test using the ethanol-inducible system based on PVX vector. Control: plants treated 2 days post-infiltration with water; ethanol-treated: plants treated 2 days post-infiltration with 4% ethanol.

The alcA-CP construct (pICH26356) was co-infiltrated with alcR (pICH18693) and a CP-deficient viral vector (pICH21692). Cell-to-cell movement can be detected only on plants treated with ethanol and no difference can be seen to a 35S promoter-CP construct (FIG. 7).

Example 8

Analysis of Plants Stably Transformed with Viral Constructs pICH18951 and pICH20592

*N. benthamiana* and *N. tabacum* plants were transformed according to standard protocols (Horsh et al., 1985, *Science*, 227, 1229-1231). Regenerated plants were analysed for the presence of the transgene by agroinfiltration with the alcR construct (pICH18693) and ethanol treatment. Indeed, most plants showed GFP-expression in the infiltrated part of the leaves and no background in other parts (FIG. 8)

Example 9

Induction of Whole Transgenic Plants

Transgenic plants containing either pICH18951 or pICH20592 (described in Example 8) were crossed with those containing the transcriptional activator alcR (pICH18693). F1 progeny of those plants were treated with ethanol either by spraying with 4% ethanol or by a combination of root drenching (with 1% ethanol) and spraying (4% ethanol). Viral amplification and thus GFP-expression is detected in almost all parts of these plants (FIG. 9). Most notably, strong expression is also detected in the stem and leaf stalks of those plants treated with root drenching. These parts of the plants usually show no or only weak expression using the standard Magnification procedure, i.e. vacuum-infiltration of whole plants (Marillonnet et al., 2005, *Nat. Biotechnol.*, 23:718-723). Spraying plants with 4% ethanol without root drenching leads to GFP expression only in soft leaf tissue, but not in the stem and leaf stalks (FIG. 10).

Example 10

Figure 12:
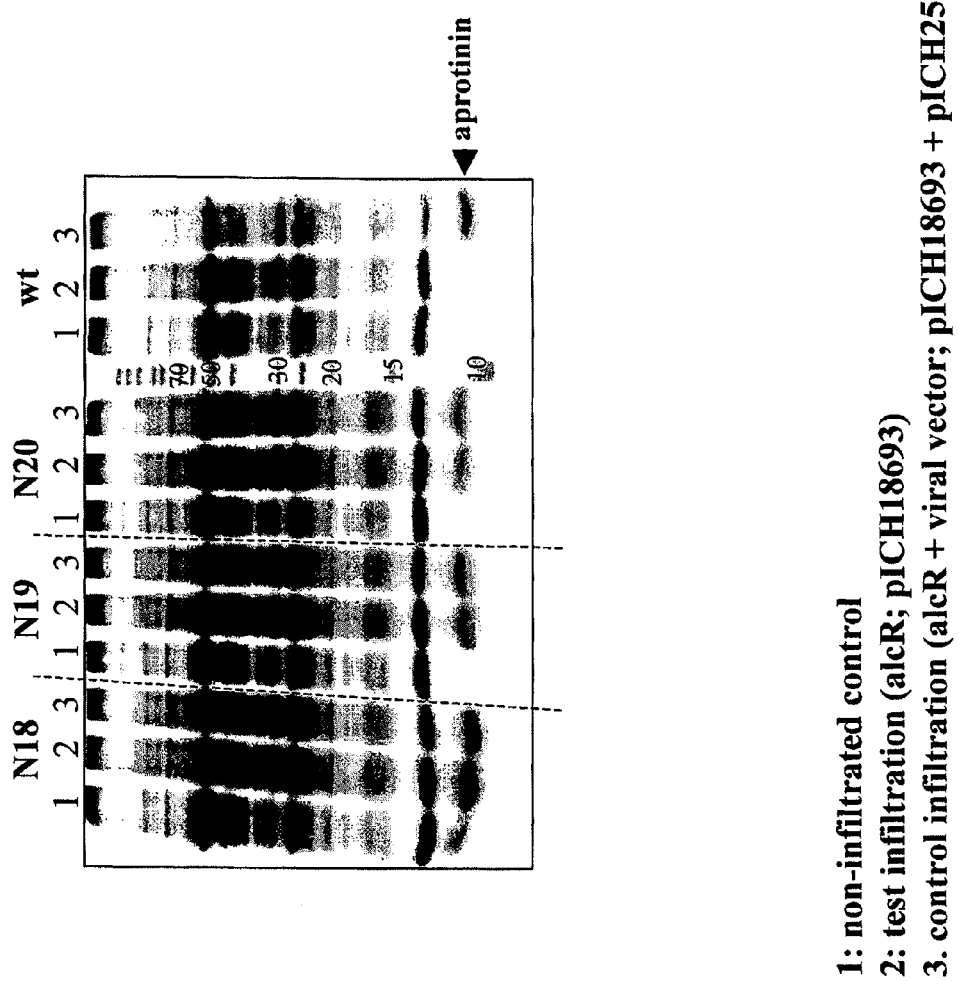
FIG. 12 shows Comassie-stained polyacrylamide gel with the results of electrophoretic analysis of total soluble protein extracted from different transgenic plants (N18, N19 and N20) carrying T-DNA region of plasmid pICH25408 with aprotinin gene.

Use of Inducible Viral Vector System for Expression of Recombinant Aprotinin in Plants Plasmid pICH25408 (FIG. 11) was designed in the way similar to plasmid pICH20592 (see EXAMPLE 5). *N. benthamiana* plants were transformed with pICH25408 according to standard protocols (Horsh et al., 1985, *Science*, 227, 1229-1231). Regenerated plants were analysed for the presence of the transgene by agroinfiltration with the alcR construct (pICH18693) and ethanol treatment followed by the analysis of recombinant protein expression by polyacrylamide gel (PAAG) electrophoresis. Part of the leaf tissue agroinfiltrated with alcR construct (pICH18693) and treated with ethanol was used for total soluble protein extraction by 2xLaemmli buffer (125 mM tris-HCl, pH 7.8, 10% β-mercaptoethanol, 20% glycerol, 0.001% bromphenol blue, 10% SDS) followed by electrophoretic separation in PAAG. Results of such analysis for different primary transformants are shown in FIG. 12.

In the next step, plants transformed with pICH25408 were crossed with plants carrying alcR gene (pICH18693). Total soluble protein isolated from leaf tissue of F1 progeny after treatment with ethanol was analysed on PAAG. The results of the analysis are shown in FIG. 13. It is evident that aprotinin is expressed at high level (about 1 mg/g of fresh leaf biomass).

The invention claimed is:

1. A process of producing one or more than one protein of interest, comprising:
   (a) providing a plant or a plant cell comprising
      (i) in a nuclear chromosome a first heterologous nucleotide sequence comprising:
         a nucleotide sequence encoding an RNA replicon, and a first chemically inducible promoter operably linked to said nucleotide sequence encoding said RNA replicon;
         said RNA replicon not encoding a protein providing for cell-to-cell movement of said RNA replicon in said plant;
         said RNA replicon encoding a polymerase for replicating said RNA replicon and said one or more than one protein of interest;
         and said RNA replicon being a plus-sense single-stranded RNA replicon derived from a plant virus of genus Potexvirus or Tobamovirus;
      (ii) a second heterologous nucleotide sequence comprising a sequence encoding a protein enabling cell-to-cell movement of said RNA replicon, wherein said second heterologous nucleotide sequence comprises a second chemically inducible promoter operably linked to said sequence encoding said protein enabling cell-to-cell movement of said RNA replicon; and
   (b) inducing, in said plant or plant cell of step (a), said first and said second chemically inducible promoter, thereby producing said one or more than one protein of interest in said plant or in said plant cell, respectively.

2. The process according to claim 1, wherein said first and said second chemically inducible promoter are inducible by the same chemical inducing signal.

3. The process according to claim 1, wherein said chemically inducible promoter is selected from the group consisting of an ethanol-inducible promoter, an IPTG-inducible promoter, and a tetracyclin-inducible promoter.

4. The process according to claim 1, wherein said plant virus of genus Potexvirus or Tobamovirus is tobacco mosaic virus or potato virus X.

5. The process according to claim 1, wherein said plant comprises a third heterologous nucleotide sequence comprising a nucleotide sequence encoding a further RNA replicon and a third chemically inducible promoter operably linked to said sequence encoding said further RNA replicon, said further RNA replicon not encoding a protein providing for cell-to-cell movement of said RNA replicon nor of said further RNA replicon in said plant, said further RNA replicon encoding a protein of interest, and wherein said further RNA replicon being a plus-sense single-stranded RNA replicon derived from a plant virus of genus Potexvirus or Tobamovirus.

6. The process according to claim 5, wherein said plant comprises a heterologous nucleotide sequence comprising a nucleotide sequence encoding a protein enabling cell-to-cell movement of said further RNA replicon operably linked to a nucleotide sequence encoding said protein enabling cell-to-cell movement of said RNA replicon.

7. The process according to claim 6, wherein said protein enabling cell-to-cell movement of said RNA replicon and said protein enabling cell-to-cell movement of said further RNA replicon are the same proteins.

8. The process according to claim 5, said further replicon encoding a polymerase for replicating said further RNA replicon.

9. The process according to claim 5, wherein said third inducible promoter is inducible by the same inducing agent as said first inducible promoter.

10. The process according to claim 5, wherein said RNA replicon and said further RNA replicon are non-competing replicons.

11. The process according to claim 10, wherein said non-competing replicons are plant viral replicons derived from plant viruses of different virus genera.

12. The process according to claim 1, wherein step (a) comprises growing a plant from a seed comprising said first heterologous nucleotide sequence.

13. A plant or plant cell comprising
   (i) in a nuclear chromosome a first heterologous nucleotide sequence comprising a nucleotide sequence encoding an RNA replicon, and a first chemically inducible promoter operably linked to said nucleotide sequence encoding said RNA replicon;
      said RNA replicon not encoding a protein providing for cell-to-cell movement of said RNA replicon in said plant;
      said RNA replicon encoding a polymerase for replicating said RNA replicon and one or more than one protein of interest;
      said RNA replicon being a plus-sense single-stranded RNA replicon derived from a plant virus of genus Potexvirus or Tobamovirus; and
   (ii) a second heterologous nucleotide sequence comprising a nucleotide sequence encoding a protein enabling cell-to-cell movement of said RNA replicon, wherein said second heterologous nucleotide sequence comprises a second chemically inducible promoter operably linked to said nucleotide sequence encoding said protein enabling cell-to-cell movement of said RNA replicon.

14. The plant or plant cell according to claim 13, belonging to the genus Nicotiana.

15. A process of producing a plant or plant cell as defined in claim 13, comprising introducing into a plant nuclear chromosome said first heterologous nucleotide sequence as defined in claim 13 and said second heterologous nucleotide sequence as defined in claim 13 and regenerating a transformed plant containing said first and said second heterologous nucleotide sequence.

16. A process of producing a plant or plant cell comprising
(i) in a nuclear chromosome a first heterologous nucleotide sequence comprising:
   a nucleotide sequence encoding an RNA replicon, and
   a first chemically inducible promoter operably linked to said nucleotide sequence encoding said RNA replicon;
   said RNA replicon not encoding a protein providing for cell-to-cell movement of said RNA replicon in said plant;
   said RNA replicon encoding a polymerase for replicating said RNA replicon and one or more than one protein of interest;
(ii) a second heterologous nucleotide sequence comprising a sequence encoding a protein enabling cell-to-cell movement of said RNA replicon, wherein said second heterologous nucleotide sequence comprises a second chemically inducible promoter operably linked to said sequence encoding said protein enabling cell-to-cell movement of said RNA replicon; and
(iii) in a nuclear chromosome a third heterologous nucleotide sequence comprising a nucleotide sequence encoding a further RNA replicon and a third chemically inducible promoter operably linked to said sequence encoding said further RNA replicon, said further RNA replicon not encoding a protein providing for cell-to-cell movement of said RNA replicon nor of said further RNA replicon in said plant, said further RNA replicon encoding a protein of interest;
said process comprising crossing a first plant comprising said first heterologous nucleotide sequence and said second heterologous nucleotide sequence with a second plant comprising said third heterologous nucleotide sequence; said RNA replicon and said further RNA replicon being plus-sense single-stranded RNA replicons derived from a plant virus of genus Potexvirus or Tobamovirus.

* * * * *

```
                    SEQUENCE LISTING

<160> NUMBER OF SEQ ID NOS: 12

<210> SEQ ID NO 1
<211> LENGTH: 26
<212> TYPE: DNA
<213> ORGANISM: Artificial Sequence
<220> FEATURE:
<223> OTHER INFORMATION: PCR primer

<400> SEQUENCE: 1
gatccatgga accagtaacg ttatac                                        26

<210> SEQ ID NO 2
<211> LENGTH: 30
<212> TYPE: DNA
<213> ORGANISM: Artificial Sequence
<220> FEATURE:
<223> OTHER INFORMATION: PCR primer

<400> SEQUENCE: 2
tctggatcct cactgcccgc tttccagtcg                                    30

<210> SEQ ID NO 3
<211> LENGTH: 55
<212> TYPE: DNA
<213> ORGANISM: Artificial Sequence
<220> FEATURE:
<223> OTHER INFORMATION: PCR primer

<400> SEQUENCE: 3
cgccatgggc cctaagaaga agaggaaggt tgaaccagta acgttatacg atgtc        55

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
aattgtgagc gctcacaatt                                               20

<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
```

```
ggaaccctgt ggttggcaca t                                          21

<210> SEQ ID NO 6
<211> LENGTH: 42
<212> TYPE: DNA
<213> ORGANISM: Artificial Sequence
<220> FEATURE:
<223> OTHER INFORMATION: PCR primer

<400> SEQUENCE: 6
cgaattgtga gcgctcacaa tttatatagg cgggtttatc tc                   42

<210> SEQ ID NO 7
<211> LENGTH: 46
<212> TYPE: DNA
<213> ORGANISM: Artificial Sequence
<220> FEATURE:
<223> OTHER INFORMATION: PCR primer

<400> SEQUENCE: 7
taaattgtga gcgctcacaa ttcgctttga agttttagtt ttattg               46

<210> SEQ ID NO 8
<211> LENGTH: 32
<212> TYPE: DNA
<213> ORGANISM: Artificial Sequence
<220> FEATURE:
<223> OTHER INFORMATION: PCR primer

<400> SEQUENCE: 8
tttctgcagg aaatgaaagg ccgcgaaaca ag                              32

<210> SEQ ID NO 9
<211> LENGTH: 28
<212> TYPE: DNA
<213> ORGANISM: Artificial Sequence
<220> FEATURE:
<223> OTHER INFORMATION: PCR primer

<400> SEQUENCE: 9
catgaattct aggattggat gcatgcgg                                   28

<210> SEQ ID NO 10
<211> LENGTH: 31
<212> TYPE: DNA
<213> ORGANISM: Artificial Sequence
<220> FEATURE:
<223> OTHER INFORMATION: PCR primer

<400> SEQUENCE: 10
cagctcgagg tcgtcctctc caaatgaaat g                               31

<210> SEQ ID NO 11
<211> LENGTH: 34
<212> TYPE: DNA
<213> ORGANISM: Artificial Sequence
<220> FEATURE:
<223> OTHER INFORMATION: PCR primer

<400> SEQUENCE: 11
cgcgcatgct actaggattg gatacatgcg gaac                            34
```

```
<210> SEQ ID NO 12
<211> LENGTH: 35
<212> TYPE: DNA
<213> ORGANISM: Artificial Sequence
<220> FEATURE:
<223> OTHER INFORMATION: PCR primer

<400> SEQUENCE: 12
tttggtctca tcaactccaa atgaaatgaa cttcc                              35
```